(12) United States Patent
Kapur et al.

(10) Patent No.: US 10,583,438 B2
(45) Date of Patent: Mar. 10, 2020

(54) COMBINED SORTING AND CONCENTRATING PARTICLES IN A MICROFLUIDIC DEVICE

(71) Applicant: The General Hospital Corporation, Boston, MA (US)

(72) Inventors: Ravi Kapur, Sharon, MA (US); Kyle C. Smith, Cambridge, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/425,818

(22) Filed: Feb. 6, 2017

(65) Prior Publication Data

US 2017/0144159 A1    May 25, 2017

Related U.S. Application Data

(63) Continuation of application No. 14/931,293, filed on Nov. 3, 2015, now Pat. No. 9,610,582.
(Continued)

(51) Int. Cl.
*G01N 3/00* (2006.01)
*G01N 3/02* (2006.01)
(Continued)

(52) U.S. Cl.
CPC ........ *B01L 3/502761* (2013.01); *A61K 35/28* (2013.01); *B01L 3/502715* (2013.01);
(Continued)

(58) Field of Classification Search
CPC ................ B01L 3/00; B01L 3/02; G01N 1/18
(Continued)

(56) References Cited

U.S. PATENT DOCUMENTS 5,968,820 A   10/1999   Zborowski et al.
6,540,896 B1   4/2003   Manz et al.
(Continued)

FOREIGN PATENT DOCUMENTS

CN   101678356   3/2010
CN   101765762   6/2010
(Continued)

OTHER PUBLICATIONS

Augustsson et al., "Microfluidic, Label-Free Enrichment of Prostate Cancer Cells in Blood Based on Acoustophoresis," Anal. Chem., 84(18):7954-7965, Sep. 2012.
(Continued)

*Primary Examiner* — Brian J. Sines
(74) *Attorney, Agent, or Firm* — Fish & Richardson P.C.

(57) ABSTRACT

Extracting and concentrating particles from a first fluid sample includes: providing the first fluid sample to a fluid exchange module of a microfluidic device, providing a second fluid sample to the fluid exchange module, in which the first fluid sample and the second fluid sample are provided under conditions such that particle-free portions of the first fluid sample are shifted, and an inertial lift force causes the particles in the first fluid sample to cross streamlines and transfer into the second fluid sample; passing the second fluid sample containing the transferred particles to a particle concentration module under conditions such that particle-free portions of the second fluid sample are shifted, and such that the particles within the second fluid sample are focused to a streamline within the particle concentration module.

25 Claims, 16 Drawing Sheets

Related U.S. Application Data

(60) Provisional application No. 62/074,315, filed on Nov. 3, 2014, provisional application No. 62/074,213, filed on Nov. 3, 2014.

(51) Int. Cl.

| | | |
|---|---|---|
| *B01L 3/00* | (2006.01) | |
| *G01N 1/18* | (2006.01) | |
| *G01N 15/02* | (2006.01) | |
| *G01N 1/40* | (2006.01) | |
| *G01N 15/14* | (2006.01) | |
| *A61K 35/28* | (2015.01) | |
| *G01N 15/06* | (2006.01) | |
| *G01N 15/00* | (2006.01) | |

(52) U.S. Cl.
CPC ... *B01L 3/502746* (2013.01); *B01L 3/502753* (2013.01); *G01N 1/4077* (2013.01); *G01N 15/0255* (2013.01); *G01N 15/0618* (2013.01); *G01N 15/1484* (2013.01); *B01L 3/502776* (2013.01); *B01L 2200/0631* (2013.01); *B01L 2200/0647* (2013.01); *B01L 2200/0652* (2013.01); *B01L 2200/0668* (2013.01); *B01L 2200/0684* (2013.01); *B01L 2200/12* (2013.01); *B01L 2300/0681* (2013.01); *B01L 2300/0877* (2013.01); *B01L 2300/185* (2013.01); *B01L 2400/043* (2013.01); *B01L 2400/0409* (2013.01); *B01L 2400/0415* (2013.01); *B01L 2400/0436* (2013.01); *B01L 2400/0457* (2013.01); *B01L 2400/0487* (2013.01); *B01L 2400/082* (2013.01); *G01N 2001/4088* (2013.01); *G01N 2015/0053* (2013.01); *G01N 2015/0065* (2013.01); *G01N 2015/0288* (2013.01); *G01N 2015/149* (2013.01); *G01N 2015/1486* (2013.01); *G01N 2015/1493* (2013.01)

(58) Field of Classification Search
USPC ......... 422/50, 68.1, 502, 503, 509; 436/180, 436/174, 177, 178
See application file for complete search history.

(56) References Cited

U.S. PATENT DOCUMENTS

| | | | |
|---|---|---|---|
| 6,632,652 B1 | 10/2003 | Austin | |
| 6,767,706 B2 | 7/2004 | Quake et al. | |
| 7,560,267 B2 | 7/2009 | Yang et al. | |
| 7,641,865 B2 | 1/2010 | Tonkovich et al. | |
| 7,837,040 B2 | 11/2010 | Ward et al. | |
| 8,021,614 B2 | 9/2011 | Huang et al. | |
| 8,186,913 B2 | 5/2012 | Toner et al. | |
| 8,906,322 B2 | 12/2014 | Huang | |
| 2002/0187503 A1 | 12/2002 | Harrold | |
| 2003/0092029 A1 | 5/2003 | Josephson et al. | |
| 2003/0124194 A1 | 7/2003 | Gaw et al. | |
| 2003/0175944 A1 | 9/2003 | Yang et al. | |
| 2003/0226806 A1 | 12/2003 | Young et al. | |
| 2004/0033515 A1 | 2/2004 | Cao et al. | |
| 2004/0053403 A1 | 3/2004 | Jedrzejewski et al. | |
| 2004/0126890 A1 | 7/2004 | Gjerde | |
| 2004/0144651 A1 | 7/2004 | Huang | |
| 2005/0109716 A1* | 5/2005 | Leach | B01L 3/502 210/787 |
| 2006/0068490 A1 | 3/2006 | Tang | |
| 2006/0078888 A1 | 4/2006 | Griffiths et al. | |
| 2006/0160243 A1 | 7/2006 | Tang et al. | |
| 2006/0269965 A1 | 11/2006 | Josephson et al. | |
| 2007/0026381 A1 | 2/2007 | Huang et al. | |
| 2007/0026419 A1 | 2/2007 | Fuchs et al. | |
| 2007/0059781 A1 | 3/2007 | Kapur et al. | |
| 2007/0099207 A1 | 5/2007 | Fuchs et al. | |
| 2007/0196820 A1 | 8/2007 | Kapur et al. | |
| 2008/0023399 A1 | 1/2008 | Inglis | |
| 2009/0032449 A1 | 2/2009 | Mueth et al. | |
| 2009/0269767 A1 | 10/2009 | Soderlund et al. | |
| 2010/0006479 A1 | 1/2010 | Reichenbach | |
| 2010/0059414 A1 | 3/2010 | Sturnn et al. | |
| 2011/0091987 A1 | 4/2011 | Weissleder et al. | |
| 2012/0037544 A1 | 2/2012 | Lane et al. | |
| 2012/0258459 A1 | 10/2012 | Huang | |
| 2013/0079251 A1 | 3/2013 | Boles | |
| 2013/0086980 A1 | 4/2013 | Gadini et al. | |
| 2013/0121895 A1 | 5/2013 | Tang et al. | |
| 2013/0168298 A1* | 7/2013 | Huang | G01N 27/44704 209/273 |
| 2013/0228530 A1 | 9/2013 | Di Carlo et al. | |
| 2014/0030788 A1 | 1/2014 | Chen et al. | |
| 2014/0093867 A1 | 4/2014 | Burke et al. | |
| 2014/0227777 A1 | 8/2014 | Choi et al. | |
| 2014/0248621 A1 | 9/2014 | Collins | |
| 2014/0342375 A1* | 11/2014 | Grisham | B01L 3/502753 435/7.24 |
| 2015/0202356 A1 | 7/2015 | Gifford | |
| 2016/0047735 A1* | 2/2016 | Grisham | G01N 15/1484 435/7.1 |
| 2016/0139012 A1 | 5/2016 | D'Silva et al. | |
| 2017/0209864 A1 | 7/2017 | Grisham et al. | |
| 2017/0225166 A1 | 8/2017 | Toner et al. | |

FOREIGN PATENT DOCUMENTS

| | | |
|---|---|---|
| CN | 102791616 | 11/2012 |
| JP | 2004-170396 | 6/2004 |
| JP | 2007-196219 | 8/2007 |
| JP | 2013-515599 | 5/2013 |
| WO | 2000/061191 | 10/2000 |
| WO | WO 2004/037374 | 5/2004 |
| WO | 2004/074814 | 9/2004 |
| WO | WO 2005/086703 | 9/2005 |
| WO | WO 2006/108087 | 10/2006 |
| WO | WO 2010/123594 | 10/2010 |
| WO | WO 2011/132164 | 10/2011 |
| WO | WO 2012/067985 | 5/2012 |
| WO | 2014/004577 | 1/2014 |
| WO | WO 2014/107240 | 7/2014 |
| WO | 2015/116990 | 8/2015 |

OTHER PUBLICATIONS

Burke et al., "High-throughput particle separation and concentration using spiral inertial filtration," Biomicrofluidics 8, 024105 (2014), 18 pages.

D'Avino et al., "Single line particle focusing induced by viscoelasticity of the suspending liquid: theory, experiments and simulations to design a micropipe flow-focuser," Lab Chip, 12(9):1638-1645, Feb. 2012.

David W. Inglis, Efficient Microfluidic Particle Separation Arrays, 013510-1 to 013510-3, Jan. 9, 2009, American Institute of Physics, Published Online.

Del Giudice et al., "Particle alignment in a viscoelastic liquid flowing in a square-shaped microchannel," Lab Chip, 2013, 13, pp. 4263-4271, Aug. 2013.

Di Carlo et al., "Continuous inertial focusing, ordering, and separation of particles in microchannels," Proc. Natl. Acad. Sci. U.S.A., 104(48):18892-18897, Nov. 2007.

Di Carlo et al., "Particle segregation and dynamics in confined flows," Phys. Rev. Lett., 102(9):094503, Mar. 2009.

Di Carlo, "Inertial microfluidics," Lab Chip, 9(21):3038-3046, Aug. 2009.

Gifford et al., "Controlled Incremental Filtration: A simplified approach to design and fabrication of high-throughput microfluidic devices for selective enrichment of particles," Lab Chip, DOI: 10.1039/C4LC00785A, Sep. 2014, 30 pages.

International Preliminary Report on Patentability in International Application No. PCT/US2015/058841, dated May 9, 2017, 16 pages.

(56) References Cited

OTHER PUBLICATIONS

International Preliminary Report on Patentability in International Application No. PCT/US2015/058834, dated May 9, 2017, 10 pages.
International Preliminary Report on Patentability in International Application No. PCT/US2015/058785, dated May 9, 2017, 6 pages.
International Search Report and Written Opinion in International Application No. PCT/US2015/058834, dated Feb. 17, 2016, 13 pages.
International Search Report and Written Opinion in International Application No. PCT/US2015/058785, dated Feb. 16, 2016, 10 pages.
International Search Report in International Application No. PCT/US2015/058841, dated Feb. 23, 2016, 5 pages.
Kang et al., "Dna-based highly tunable particle focuser," Nature Communications, 4:2567, Oct. 2013, 8 pages.
Lee et al., "Dynamic self-assembly and control of microfluidic particle crystals," Proceedings of the National Academy of Sciences, 107(52):22413-22418, Nov. 2010.
Lee et al., "Multiplex Particle Focusing via Hydrodynamic Force in Viscoelastic Fluids," Scientific Reports, 3:3258, Nov. 2013, 8 pages.
Lim et al., "Inertio-elastic focusing of bioparticles in microchannels at high throughput," Nature Communications, (5:4120), pp. 1-9, Jun. 2014.
Martel and Toner, "Inertial Focusing in Microfluidics," Annual Review of Biomedical Engineering, 16:371-396, Jul. 2014.
Martel and Toner, "Particle Focusing in Curved Microfluidic Channels," Scientific Reports, 3(3340):1-8, Nov. 2013.
Office Action in U.S. Appl. No. 14/931,223, dated May 19, 2017, 15 pages.
Office Action in U.S. Appl. No. 14/931,421, dated May 19, 2017, 19 pages.
Peterson et al., "Bacterial Cell Surface Damage Due to Centrifugal Compaction," Applied and Environmental Microbiology, 78(1):120-125, Jan. 2012.
Shen et al., "High-throughput rare cell separation from blood samples using steric hindrance and inertial microfluidics," Lab Chip, 2014, DOI: 10.1039/C3LC51384J, Mar. 2014, 15 pages.
Tanyeri et al., "A microfluidic-based hydrodynamic trap: Design and implementation," Lab Chip, 11(10):1786-1794, May 2011.
Yang et al., "Sheathless elasto-inertial particle focusing and continuous separation in a straight rectangular microchannel," Lab Chip, 11(2):266-273, Jan. 2011.
Extended European Search Report in Application No. 15856708.1, dated May 16, 2018, 9 pages.
Office Action in U.S. Appl. No. 14/931,421, dated Oct. 4, 2017, 15 pages.
Written Opinion in International Application No. PCT/US2015/058841, dated Feb. 23, 2016, 14 pages.
Extended European Search Report in Application No. 15856773.5, dated Apr. 20, 2018, 9 pages.
Extended European Search Report in Application No. 15856423.7, dated Apr. 20, 2018, 8 pages.
Office Action in Japanese Application No. 2017-523990, dated Dec. 18, 2018, 10 pages (with English translation).
Office Action in Chinese Application No. 201580071263.4, dated Apr. 2, 2019, 34 pages (with English tmnslation).
Office Action in Chinese Application No. 201580069630.7, dated Apr. 2, 2019, 23 pages (with English tmnslation).
Office Action in Chinese Application No. 201580071415.0, dated Apr. 2, 2019, 26 pages (with English tmnslation).
Lubbersen et al., "Visualization of inertial flow in deterministic ratchets", Separation and Purification Technology 109 (2013) 33-39.
Lubbersen et al., "High throughput particle separation with a mirrored deterministic ratchet design", Chemical Engineering and Processing 77 (2014) 42-49.
Loutherback, "Microfluidic Devised for High Throughput Cell Sorting and Chemical Treatment", Dissertation, Nov. 2011.
Office Action in Indian Application No. 201737018682, dated May 22, 2019, 6 pages.
Office Action in Japanese Application No. 2017-523990, dated Jun. 7, 2019, 7 pages (with English translation).
EP Office Action in European Application No. 15856773.5, dated Dec. 2, 2019, 6 pages.

* cited by examiner

WBC Yield

COMBINED SORTING AND CONCENTRATING PARTICLES IN A MICROFLUIDIC DEVICE

CROSS-REFERENCE TO RELATED APPLICATIONS

This application is a continuation application of U.S. application Ser. No. 14/931,293, filed Nov. 3, 2015, which claims the benefit of U.S. Provisional Application No. 62/074,213, filed Nov. 3, 2014, and U.S. Provisional Application No. 62/074,315, filed Nov. 3, 2014, each of which is incorporated herein by reference in its entirety.

TECHNICAL FIELD

The present disclosure relates to combined sorting and concentrating, or vice versa, of particles in a microfluidic device.

BACKGROUND

Particle separation and filtration have been used in numerous applications across industries and fields. Examples of such applications include chemical process and fermentation filtration, water purification/wastewater treatment, sorting and filtering components of blood, concentrating colloid solutions, and purifying and concentrating environmental samples. Various macro-scale techniques have been developed for use in these applications including methods such as centrifugation and filter-based techniques. Typically, such techniques require systems that are large, bulky, and expensive and have complex moving components.

In certain cases, micro-scale techniques offer advantages over macro-scale techniques, in that scaling down allows the use of unique hydrodynamic effects for particle sorting and filtration, and thus eliminates the need for large systems with complex moving components. Moreover, micro-scale techniques offer the possibility of portable devices capable of performing sorting and filtration at much lower cost than larger macro-scale systems. However, typical micro-scale sorting and filtration devices can be limited in the amount of fluid they can handle over a specified period of time (i.e., low throughput), potentially placing such devices at a disadvantage to their macro-scale counterparts.

SUMMARY

The present disclosure is based, at least in part, on the discovery that if one carefully controls the geometries and dimensions of microfluidic devices one can not only transfer particles between different fluid samples, but also substantially alter the concentration of particles within a particular fluid sample. In particular, microfluidic devices are disclosed that employ two separate microfluidic modules, e.g., integrated on a single chip or substrate, in which one module uses an array of island structures to process a source fluid sample (e.g., to transfer particles from the source fluid to a separate second fluid) based on a combination of inertial lift forces and fluid shifting, and in which a second module also uses fluid shifting in combination with inertial focusing to enhance or increase the concentration of the particles, e.g. particles transferred to the second fluid sample. By placing many of each type of module in parallel, an ultra-high throughput microfluidic device can be obtained. The modules can be arranged in any order, e.g., various modules can be arranged in any order in series and/or in parallel.

In general, in one aspect, the subject matter of the present disclosure can be embodied in a microfluidic device that includes: a first fluid sample input port; a fluid sample input port; a fluid exchange module in a first substrate, the fluid exchange module comprising a corresponding first microfluidic channel and a first array of island structures in the first microfluidic channel, the first array of island structures being arranged in one or more rows that extend along a longitudinal direction of the first microfluidic channel, each island structure in a row being spaced apart from an adjacent island structure in the row to form an opening, in which the first array of island structures in each fluid exchange module is configured and arranged to shift portions of fluid through the opening between adjacent island structures within a row; and a particle concentration module in a second substrate, the particle concentration module that includes a corresponding second microfluidic channel and a second array of island structures, each island structure in the second array being spaced apart from an adjacent island structure to form an opening, in which the second array island structures in each particle concentration module is configured and arranged to shift portions of the product fluid through the opening between adjacent island structures in the second array toward a first side of the second array of island structures, and to focus particles contained within the product fluid along one or more streamlines on a second opposite side of the second array of island structures.

Implementations of the device can have one or more of the following features. For example, in some implementations, an output of the first microfluidic channel of the fluid exchange module is fluidly coupled to an input of the second microfluidic channel of the particle concentration module. The fluid exchange module can be arranged to receive in the first microfluidic channel a first fluid sample from the first fluid sample input port and a second fluid sample from the second fluid sample input port.

In some implementations, an output of the second microfluidic channel of the particle concentration module is fluidly coupled to an input of the first microfluidic channel of the fluid exchange module. The particle concentration module can be arranged to receive in the second microfluidic channel a first fluid sample from the first fluid sample input port, in which the fluid exchange module is arranged to receive in the first microfluidic channel a second fluid sample from the second fluid sample input port.

In some implementations, the first substrate and the second substrate are the same substrate.

In some implementations, the first array of island structures in each fluid exchange module is configured and arranged to shift portions of fluid through the opening between adjacent island structures within a row due to reduced fluidic resistance beyond the opening, and the second array island structures in each particle concentration module is configured and arranged to shift portions of the product fluid through the opening between adjacent island structures in the second array toward a first side of the second array of island structures due to reduced fluidic resistance beyond the opening.

In some implementations, for the fluid exchange module, a distance between a first wall of the first microfluidic channel and the first array of island structures progressively increases along the longitudinal direction of the first microfluidic channel. For the fluid exchange module, a distance between a second wall of the first microfluidic channel and the first array of island structures can progressively decrease along the longitudinal direction of the microfluidic channel.

In some implementations, for the particle concentration module, a distance between a first wall of the second microfluidic channel and the second array of island structures progressively increases along the longitudinal direction of the second microfluidic channel. For the particle concentration module, the second array of island structures and a second wall of the second microfluidic channel can be arranged and configured to define an undulating fluid pathway between the island structures of the second array and the second wall along the longitudinal direction of the second microfluidic channel. A curvature of the second wall can alternate between regions of high curvature and regions of low curvature. Each island structure within the second array of island structures can include a triangular prism.

In some implementations, the device includes: multiple fluid exchange modules arranged in parallel; and multiple particle concentration modules arranged in parallel.

In some implementations, the microfluidic device includes a filter, the filter being fluidly coupled to the first fluid sample input port and fluidly coupled to either the fluid exchange module or the particle concentration module arranged downstream from the filter, in which each filter includes an array of post structures.

In some implementations, the microfluidic device includes a filter, the filter being fluidly coupled to one of the fluid exchange module or the particle concentration module arranged upstream of the filter and to the other of the fluid exchange module or the particle concentration module arranged downstream of the filter, in which the filter includes an array of post structures.

In some implementations, the microfluidic device includes an inertial concentrator, the inertial concentrator being fluidly coupled to either the fluid exchange module or the particle concentration module arranged upstream of the inertial concentrator and fluidly coupled to the other one of the fluid exchange module or the particle concentration module arranged downstream of the inertial concentrator, in which the inertial concentrator includes a third microfluidic channel having a cross-section transverse to a longitudinal direction of the third microfluidic channel, and in which a size of the cross-section periodically increases and decreases along the longitudinal direction of the third microfluidic channel.

In another aspect, the subject matter of the present disclosure can be embodied in a method of extracting and concentrating particles from a first fluid sample, the method including: providing the first fluid sample to a fluid exchange module of a microfluidic device; providing a second fluid sample to the fluid exchange module of the microfluidic device, the fluid exchange module including a corresponding first microfluidic channel and a first array of island structures in the first microfluidic channel, the first array of island structures being arranged in one or more rows that extend along a longitudinal direction of the first microfluidic channel, each island structure in a row being spaced apart from an adjacent island structure in the row to form an opening, in which the first fluid sample and the second fluid sample are provided to the fluid exchange module under conditions such that particle-free portions of the first fluid sample are shifted through the opening between adjacent island structures within a row, and an inertial lift force causes the particles in the first fluid sample to cross streamlines and transfer into the second fluid sample; passing, from the fluid exchange module, the second fluid sample containing the transferred particles, to a particle concentration module, the particle concentration module comprising a corresponding second microfluidic channel and a second array of island structures arranged in a row, each island structure within the second array being spaced apart from an adjacent island structure in the row to form an opening, in which the second fluid sample containing the transferred particles is provided to the particle concentration module under conditions such that particle-free portions of the second fluid sample are shifted through the opening between adjacent island structures within the second microfluidic channel, and such that the particles within the second fluid sample are focused to one or more streamlines within an inertial focusing section of the particle concentration module.

Implementations of the method can have one or more of the following features. For example, in some implementations, the first fluid sample is whole blood and the second fluid sample is a buffer solution.

In some implementations, the particles are white blood cells. The white blood cells can be neutrophils.

In some implementations, the method further includes filtering the first fluid sample prior to providing the first fluid sample to the fluid exchange module.

In some implementations, the method further includes: passing, from the fluid exchange module, the second fluid sample containing the transferred particles to a filter; and filtering the second fluid sample in the filter prior to passing the second fluid sample to the particle concentration module.

In some implementations, the method further includes focusing, for the second fluid sample output from the fluid exchange module, the particles to one or more streamlines within the second fluid sample in a third microfluidic channel prior to passing the second fluid sample containing the transferred particles to the particle concentration module, in which, for the second fluid sample, the one or more streamlines at an output of the third microfluidic channel are aligned to an inertial focusing side of the particle concentration module.

In some implementations, the method further includes obtaining at an output of the particle concentration module a portion of the second fluid sample containing a higher concentration of the particles relative to a concentration of the particles in the second fluid sample at an input to the particle concentration module. The particle concentration within the second fluid sample at the output of the particle concentration module can be between 10 times and 100 times more than the particle concentration within the second fluid sample at the input of the particle concentration module.

Implementations of the subject matter described herein provide several advantages. For example, in some implementations, the microfluidic systems and methods described herein can be used to isolate particles within a continuously flowing fluid, increase the concentration of particles within a continuously flowing fluid without the need for centrifugation, and/or obtain purified fluid samples with low particle concentration. In some implementations, the microfluidic systems and methods described herein can be used to shift particles from one fluid to another fluid, e.g., from whole blood to a buffer solution. The continuous flow microfluidic techniques described herein offer high volumetric capacity and throughput, substantial and tunable fluid volume reduction, and high particle yields with inexpensive and simple instruments that can be implemented into various point-of-care devices. In particular, the presently described techniques offer significant advantages over existing centrifugation techniques, especially in applications where the size and expense of centrifugation is prohibitive. In some implementations, the presently described techniques also provide streamlined processing and simple integration with other microfluidic modules. For clinical applications, the systems described herein can be configured as both self-contained and disposable. In contrast, for bioprocessing/industrial applications, the devices can be configured for continuous flow/processing.

For the purposes of this disclosure, a "sample" (sometimes referred to as "fluid" or "fluid sample") is capable of flowing through a microfluidic channel. The sample can include one or more of a fluid suspension or any sample that can be put into the form of a fluid suspension, and that can flow or be driven through the microfluidic channel.

For the purposes of this disclosure, a fluid can include any type of fluid, e.g., liquid or gas. The fluid can include industrial fluids, environmental fluids or fluids used by other entities that disperse particles in such fluids for industrial or other types of processing. For example, the fluids can include oils or aqueous solutions. The fluid can include biological fluids, e.g., whole blood, plasma, buffy coat, cerebrospinal fluid, bone marrow aspirate, peritoneal, branchioalveolar, ascites, urine, or other bodily fluids. Particles contained in the fluid can include biological particles, e.g., circulating tumor cells, red blood cells, white blood cells, bone marrow cells, bacteria, fungi, virus, algae, any prokaryotic or eukaryotic cells, sperm, eggs, organelles, exosomes, or other types of biological particles that occur either naturally or are introduced artificially into the fluid. The particles can include droplets, bubbles, pollutants, precipitates, organic and inorganic particles, beads, bead labeled analytes, magnetic beads, and/or magnetically labeled analytes.

For the purposes of this disclosure, the term channel refers to a structure in which a fluid can flow.

For the purposes of this disclosure, the term microfluidic system refers to a fluidic system, device, channel, or chamber that generally has at least one cross-sectional dimension in the range of about 10 nm to about 5 mm.

For the purposes of this disclosure, the terms gap or opening refer to an area in which fluids or particles can flow. For example, a gap or opening can be a space between two obstacles through which fluids flow.

For the purposes of this disclosure, the term rigid island structure refers to a physical structure through which a particle generally cannot penetrate.

For the purposes of this disclosure, the term volume reduction means processing a suspension of cells/particles such that the product of the process has a higher concentration (and therefore smaller volume) of the cells/particles than the input.

For the purposes of this disclosure, the term a particle-free layer is understood to be an elongated region of a continuously flowing fluid sample within a microfluidic device that is substantially free of one or more different types of particles.

For the purposes of this disclosure, the term absolute particle yield is understood to mean the total number of particles in the product divided by the total number particles in the input.

For the purposes of this disclosure, the term relative yield is understood to mean the total number of particles in the product divided by the total number of particles in the output (i.e., product plus waste).

For the purposes of this disclosure, the term length fraction is understood to mean the fraction of that stream occupied by particles (as opposed to space between particles).

For the purposes of this disclosure, the term fluidic resistance refers to the ratio of pressure drop across a channel (e.g., a microfluidic channel) to the flow rate of fluid through the channel.

Particles within a sample can have any size which allows them to be ordered and focused within the microfluidic channel. For example, particles can have an average hydrodynamic size that is between 1 µm and 100 µm. The particle size is limited only by channel geometry; accordingly, particles that are larger and smaller than the above-described particles and focused with the microchannel can be used. The size of particles (e.g., cells, eggs, bacteria, fungi, virus, algae, any prokaryotic or eukaryotic cells, organelles, exosomes, droplets, bubbles, pollutants, precipitates, organic and inorganic particles, magnetic beads, and/or magnetically labeled analytes), such as the average hydrodynamic particle size or average diameter, can be determined using standard techniques well known in the field.

In some implementations, multiple particles within a fluid can be focused along a streamline of the fluid.

In some implementations, inertial focusing (sometimes referred to as "localizing") of a particle to a streamline can be achieved by varying a flow rate of a fluid carrying suspended particles flowed through a channel of constant cross-section. In some implementations, focusing can be achieved by a reduction in the area of a cross-section of a channel through which a flux of particles passes. Particles can be localized within an area having a width of, e.g., 1.05, 2, 3, 4, or 5 times the width of the particles. Localization can occur at any location within the channel, e.g., at an unobstructed portion of the channel. Localization can occur in a portion of the channel having less than 50%, 40%, 30%, 20%, 10%, 5%, 2%, 1%, or 0.1% reduction in cross-sectional area.

Unless otherwise defined, all technical and scientific terms used herein have the same meaning as commonly understood by one of ordinary skill in the art to which this invention belongs. Although methods, materials, and devices similar or equivalent to those described herein can be used in the practice or testing of the present invention, suitable methods, materials and devices are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features, objects, and will be apparent from the description, drawings, and claims.

DETAILED DESCRIPTION

Overview of Combined Microfluidic Particle Sorter and Concentrator

Figure 1:
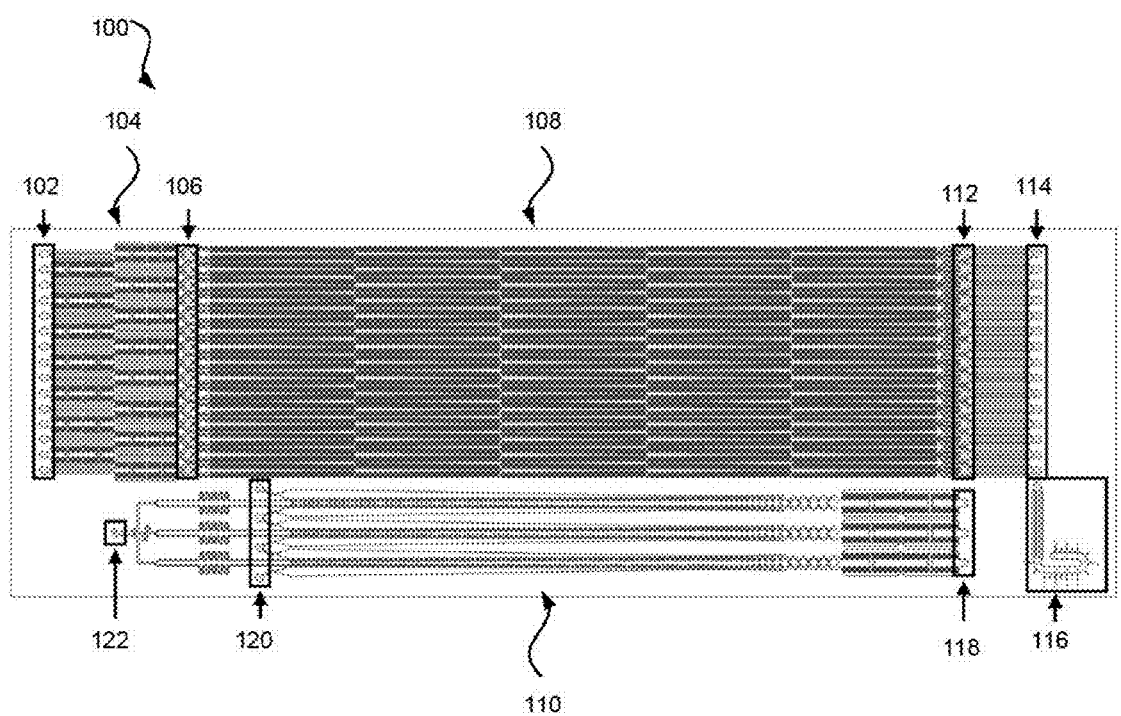
FIG. 1 is a top view of the general architecture of a representative microfluidic device according to the present disclosure.

FIG. 1 is a schematic that illustrates a top view of the general architecture of a representative microfluidic device 100 according to the present disclosure. In particular, the schematic illustrates, among other things, the outlines of various microfluidic channels, ports, reservoirs, and output receptacles for receiving, transporting, shifting, adjusting and/or storing fluid samples. The device 100 is designed to receive a fluid sample, e.g., blood, containing a suspension of one or more different types of particles, in a fluid exchange module to isolate a subpopulation of particles from the bulk fluid (e.g., by extracting and transferring one or more types of particles from the fluid sample to a second different solution), and then enrich the concentration of the extracted subpopulation of particles for subsequent analysis and processing in a particle concentration module. Alternatively, the fluid, e.g., if dilute, can first be passed through the particle concentration module and then through the fluid exchange module. The various channels, ports and reservoirs, among other structures for manipulating fluids and particles, are fabricated within a single device layer. A surface of the device layer is sealed with a lid layer (not shown in FIG. 1) that serves as a cover to the channels and reservoirs of the device layer. An optional manifold layer (not shown in FIG. 1) can be arranged on a surface of the lid layer to provide simultaneous fluidic coupling of the various through-holes to a macroscopic output/input connection (e.g., tubing). For example, all modules can be arranged and fixed on and/or fabricated on the same substrate, or each module can be arranged and fixed on and/or fabricated on individual substrates and then connected via fluid conduits and/or mechanical connections of the substrates.

The microfluidic device 100 can be sub-divided into separate sections referenced as follows: a fluid sample receiving section 102, a fluid sample filter section 104, a buffer sample receiving section 106, a fluid exchanger module (also referred to herein as a fluid force fractionation (FFF) module or an inertial exchanger) 108, a particle concentration module (also referred to herein as an inertial concentrator) 110, a fluid exchanger module product receptacle section 112, a fluid exchanger module waste receptacle section 114, a fluid exchanger module waste reservoir 116, a particle concentration module input section 118, a particle concentration module waste section 120, and a particle concentration module product output section 122. An overview of how the device 100 operates will be provided first, followed by a discussion of the different sections in detail.

In a first step, a fluid sample containing one or more different types of particles enters the chip through the fluid sample receiving section 102. The fluid sample receiving section 102 can include a series of holes into which the fluid sample can be introduced. For instance, each hole can be coupled to corresponding tubing through which the fluid sample is delivered. Alternatively, or in addition, the fluid sample receiving section 102 can include valves that can be opened and closed manually or through an automated process to control over the delivery of the fluid sample to the device 100. Other mechanisms for introducing fluid samples to a microfluidic device as known by those of ordinary skill in the art can also be utilized. The fluid sample can be driven into the device 100 using, e.g., a pump system that applies pressure to the fluid sample and enables continuous flow of the sample through the device 100.

Upon receiving the fluid sample in the device 100, the fluid sample passes to the fluid sample filter section 104 that is configured to filter particles contained in an incoming fluid according to the particle size (e.g., average diameter), such that only particles of a pre-defined size or less are able to pass to the next stage of the system. At the end of the filter section 104, the device 100 includes a buffer sample receiving section 106 configured to receive a second fluid sample (referred to as a buffer sample or buffer stream for the purpose of the example device 100). The buffer sample receiving section 106 includes multiple holes for receiving the buffer sample, in which the holes are arranged just upstream of the fluid exchanger module 108. Similar to the fluid sample receiving section, each hole can be coupled to corresponding tubing through which the fluid sample is delivered. Alternatively, or in addition, the buffer sample receiving section 106 can include valves that can be opened and closed manually or through an automated process to control over the delivery of the buffer fluid sample to the device 100.

In some embodiments, both the filtered fluid sample and the buffer fluid sample then enter the fluid exchanger module 108. In other embodiments, the filtered fluid sample and the buffer fluid sample first enter the particle concentration module. The buffer and fluid sample propagate within the fluid exchanger module 108 under conditions that enable laminar flow. That is, the fluids flow under conditions such that there is no turbulent mixing between the buffer and fluid sample. Rather, both the buffer and fluid sample propagate substantially side by side as parallel streams over the length of the fluid exchanger module 108. While in the module 108, at least a first type of particles are transferred from the fluid sample to the buffer sample so that by the end of the module 108 most, if not all, of the at least first type of particles have been extracted from the fluid sample. As will be explained, the process of transferring particles from the sample fluid to the buffer can rely, in part, on a combination of extracting the fluid sample at openings between island structures within the module 108, as well as inertial lift forces, which force particles away from the extracted fluid and into the buffer sample. Because the inertial lift force is size-dependent, it can be employed to fractionate (e.g., sort) particles based on size. Fractionation is accomplished by repeatedly (1) using the inertial lift force to move large particles away from a channel wall and then (2) shifting the fluid that is free of the large particles into an adjacent channel. After many iterations, the large particles can be moved from the source fluid (e.g., the fluid sample) across streamlines into an adjacent destination fluid (e.g., the buffer fluid sample).

At the end of the fluid exchanger module 108, the fluid sample enters the fluid exchanger module waste station 114. Though referred to as a "waste station," the fluid sample can be disposed of, re-used for other purposes or processed for further analysis.

On the other hand, the buffer fluid sample, which now contains the transferred particles, enters the fluid exchanger product receptacle section 112. In the present example, the fluid exchanger product receptacle section 112 includes through-holes into which the particle-containing buffer sample passes out of the device 100 and into a manifold layer (not shown) that directs the buffer sample back into the device 100 at the particle concentration module input section 118. In alternative implementations, the buffer sample containing the transferred particles can be fluidly coupled directly to the particle concentration module 110 without having to exit and re-enter the device 100.

The particle concentration module 110 contains three regions: a filter region, a focusing region, and a concentrator region. Upon entering the module 110, the buffer sample containing the particles propagates through the filter region, where the filter region is configured to filter particles contained in an incoming fluid according to the particle size (e.g., average diameter), such that only particles of a predefined size or less are able to pass to the next stage of the system. The buffer sample then passes to the focusing region. The focusing region employs structures that are configured to induce inertial focusing of the particles within the buffer sample along one or more streamlines. By focusing the particles along defined streamlines, the particles can be positioned at precise locations prior to entering the concentrator region, which enables, in certain implementations, the concentrator to more effectively enrich the particle concentration within the buffer sample. The concentrator region contains an array of structures configured and arranged to increase the concentration of the particles within the buffer. In particular, the particles within the buffer are subject to inertial lift forces that cause them to migrate across fluid streamlines toward equilibrium positions within the channel cross-section. Concentration of the particles is accomplished by repeatedly (1) using the inertial lift forces to move the particles away from channel walls and then (2) shifting or siphoning particle-free buffer sample into an adjacent channel. This results in two fluid outputs from the particle concentration module 110: an enriched buffer solution containing a high concentration of the extracted particles and a particle-free buffer sample.

At the end of the particle concentration module 110, the enriched buffer fluid passes to the particle concentration module product output 122, where it can be collected for further analysis and/or processing. The particle-free buffer sample passes to the waste section 120. Each of the fluid exchanger module 108 and the particle concentration module 110 employ multiplexing to establish an ultra-high throughput device capable of processing large amounts of sample fluid to obtain highly concentrated subpopulations of particles over relatively short time periods.

Sample Receiving and Filter Section

Figure 2:
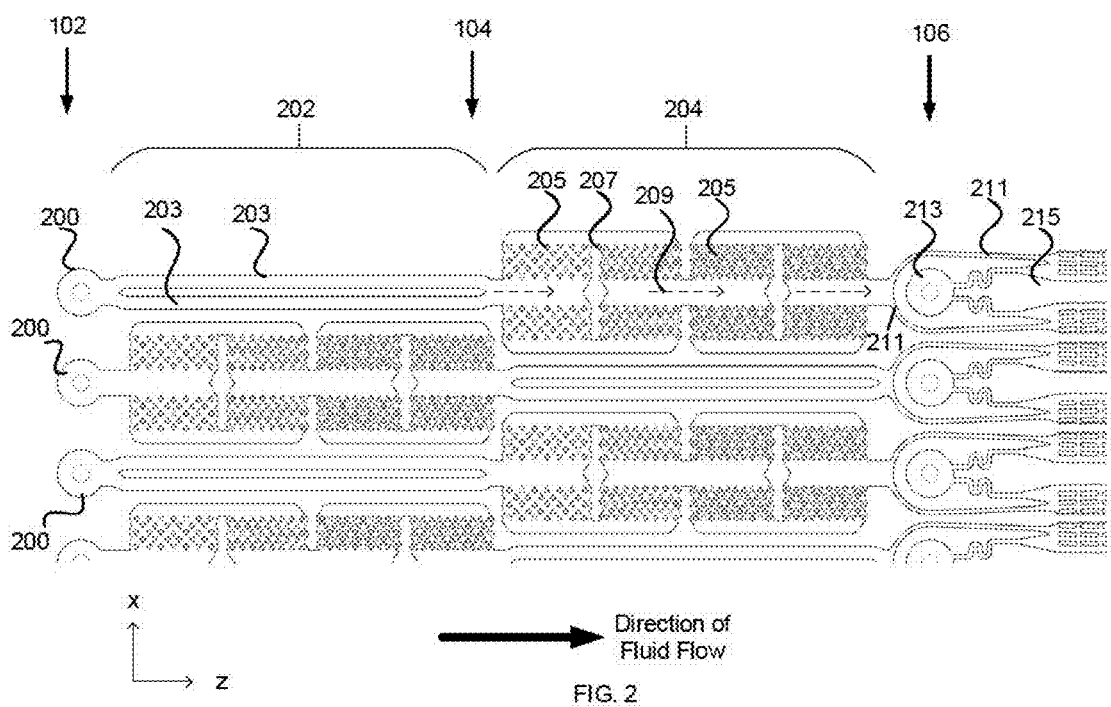
FIG. 2 is a schematic that illustrates a top view of a portion of the fluid sample receiving sections, the fluid sample filter sections, and the buffer sample receiving sections of the device shown in FIG. 1.

FIG. 2 is a schematic that illustrates a top view of a portion of the fluid sample receiving sections 102, the fluid sample filter sections 104, and the buffer sample receiving sections 106 of the device 100. To increase the microfluidic device throughput, the foregoing sections are replicated multiple times on the chip. In the present example, the sections are arranged in parallel. As explained above, the fluid sample receiving section 102 includes multiple through-holes 200 into which the fluid sample can be introduced. Each through-hole 200 can be coupled, e.g., at one end to a corresponding tubing through which the fluid sample is delivered. Alternatively, in some implementations, the device 100 includes a separate manifold layer (not shown) that is located above the through-holes 200 and that is configured to simultaneously fluidly couple each of the through-holes 200 to a single macroscopic input connection (e.g., tubing). Alternatively, or in addition, the fluid sample receiving section 102 can include valves that can be opened and closed manually or through an automated process to control over the delivery of the fluid sample to the device 100. Other mechanisms for introducing fluid samples to a microfluidic device as known by those of ordinary skill in the art can also utilized. The fluid sample can be driven into the device 100 using, e.g., a pump system that applies pressure to the fluid sample and enables continuous flow of the sample through the device 100.

From each through-hole 200, the fluid sample passes to a corresponding fluid sample filter section 104. In the present example, each fluid sample filter section 104 includes a first region 202 containing two separate straight channels 203, arranged in parallel, through which the fluid sample propagates. At the end of the two channels 203, the fluid sample merges again and flows into the second region 204 of the filter 104. Although two parallel channels are shown in each filter section 104 in FIG. 2, the first region 202 can include a single microfluidic channel or more than two microfluidic channels.

Each filter section 104 also includes the second region 204 fluidly coupled to the first region 202, in which the second region 204 contains multiple islands or post structures 205 arranged in one or more staggered arrays that act as filters for the fluid sample. The array of post structures 205 in the second region 204 are arranged and configured to filter particles contained in the fluid sample according to the particle size (e.g., average diameter), such that only particles of a pre-defined size or less are able to pass to the next stage of the system. For instance, in the case the fluid sample contains complex matrices, such as bone marrow aspirate, the array of posts 205 can be configured to remove bone chips and fibrin clots to improve the efficiency of device operations to be performed downstream (e.g., enriching particle concentration within a fluid and/or transferring particles from one fluid to another fluid). In the example arrangement shown in FIG. 2, the posts 205 within the second region 204 have a substantially triangular prism shape, in which the pillar size (e.g., approximate diameter across the short face of each pillar) and array offset spacing are designed to deflect particles above a certain size, thereby separating them from the main suspension. Typically, the size limit is determined based on the maximum particle size that is desired to pass through later stages of the device 100. For example, the array of posts 205 can be configured to filter/block passage of particles that have an average diameter greater than 50%, greater than 60%, greater than 70%, greater than 80% or greater than 90% of the minimum width of a microfluidic channel in the subsequent fluid exchanger module 108.

In the particular example shown in FIG. 2, the fluid sample enters region 204 generally along the direction indicated by arrow 209 until the fluid sample comes into contact with a wall/divider 207 that forces the fluid to propagate through the openings between posts 205, which function to filter the fluid sample. The fluid sample is forced around the wall/divider 207 passing through another one or more arrays of posts 205 and then continuing on in the direction of arrows 209. Any number or arrangement of such post arrays can be included in the filter section 104 to achieve the desired level of fluid sample filtering. Furthermore, the order in which the first and second regions of the filter section 104 are arranged is not vital to the operation of the device 100. That is, the first region 202 containing the straight channels can be arranged upstream or downstream of the second region 204 containing the post arrays 205 so long as the two regions are fluidly coupled together. For instance, as shown in FIG. 2, the order in which the first and second regions 202, 204 of the filter section 104 are arranged alternates for each through-hole 200 in order to enable tighter packing of the microfluidic channels on the chip.

Following the fluid sample filter section 104, the filtered fluid sample passes into channels 211 to create multiple streams that are fluidly coupled to fluid exchanger module 108. At the entrance to the fluid exchanger module 108, the filtered fluid sample streams propagate side by side with a second fluid (e.g., a buffer fluid sample). The buffer fluid sample enters the device in buffer sample receiving sections 106, which each include a through-hole 213 for receiving the buffer fluid sample. Similar to through-holes 200, the through-holes 213 can be fluidly coupled at one end to a corresponding tubing through which the buffer sample is delivered. Alternatively, in some implementations, a separate manifold layer (not shown) can be used to introduce fluid to each of the through-holes 213. The through-holes 213 are arranged upstream of the entrance to the fluid exchanger module 108. Buffer fluid entering from through-holes 213 is split into multiple fluid streams, one for each filtered fluid sample stream. In some cases, the buffer fluid passes through a fluid resistor that ensures the correct flow ratio between the filtered fluid sample and the buffer sample. For instance, in the present example shown in FIG. 2, the buffer sample streams each pass through a sinusoidal-like channel that functions to increase the fluid resistance.

A wall or other divider 215 maintains separation between each pair of buffer sample/fluid sample streams. Both the filtered fluid sample and the buffer propagate under conditions that promote laminar flow, such that any mixing between the sample and buffer is limited to that due to diffusion. Given the location at which the buffer fluid stream enters the fluid exchanger module 108, the buffer fluid stream propagates closest to the wall/divider 215 whereas the filtered fluid sample propagates furthest away from the wall/divider 215.

Fluid Exchanger Module

Figure 3:
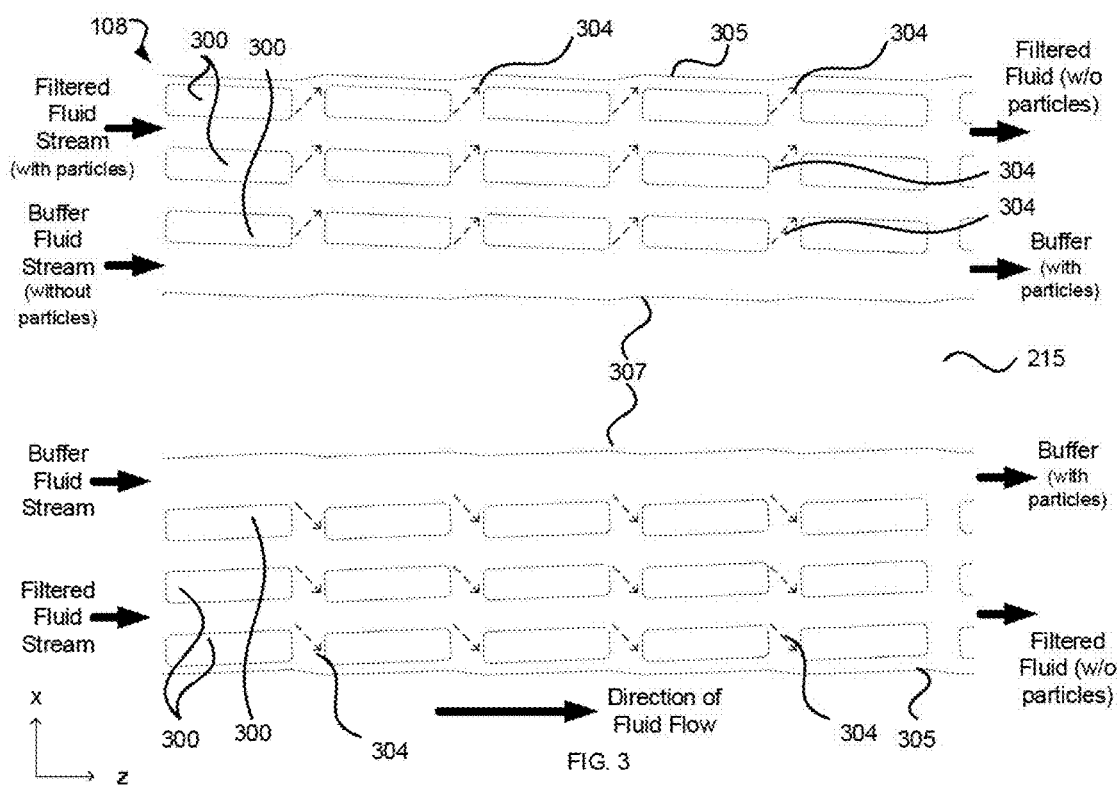
FIG. 3 is a schematic that illustrates a top view of a portion of the fluid exchange module of the device shown in FIG. 1.

FIG. 3 is a schematic that illustrates a top view of a portion of the fluid exchanger module 108. The purpose of fluid exchanger module 108 is to deplete the filtered fluid sample of large particles. That is, the fluid exchanger module 108 is configured to sort a desired sub-population of particles (e.g., relatively large particles) from the filtered fluid sample and transfer those particles to the buffer solution. Thus, the fluid exchanger module 108 "exchanges" the fluid in which the desired particles are suspended. This process also can be referred to as "fractionation." To fractionate the filtered fluid sample, the fluid exchanger 108 includes multiple island structures 300 arranged in one or more arrays, in which each island 300 is separated from an adjacent island in the array by a gap through which fluid can flow. In the example shown in FIG. 3, the fluid exchanger module 108 actually includes two separate arrays, each having three rows of islands 300, in which the arrays are separated from one another by the wall/divider 215. The islands 300 are illustrated as substantially rectangular structures with their elongated sides extending generally in the same direction as fluid flow, though other shapes and orientations can be used instead. Furthermore, the number of rows of islands and the number of island arrays can also be varied from one or more depending on the desired configuration.

Fractionation using the fluid exchanger module 108 is accomplished by repeatedly (1) shifting or extracting portions of the filtered fluid sample that are free from particles through the gaps between the islands, while simultaneously relying on (2) inertial lift forces to move particles within the fluid sample away from the locations where the fluid is extracted. After multiple iterations, the particles in the filtered fluid sample can be moved across fluid streamlines and into a second different fluid propagating alongside the fluid sample (e.g., into the buffer). The inertial forces within the fluid arise from particles flowing at relatively high speeds near microfluidic channel walls. Thus, for example, when the fluid sample propagates near the walls of the islands 300, the particles within the fluid sample will experience inertial forces pushing the particles away from the islands. Fluid extraction or shifting, on the other hand, is controlled by the relative fluidic resistance encountered by the fluid as it propagates through the arrays. For a microfluidic channel in which the fluidic resistance varies over the length of the channel, fluid will tend to follow in a direction towards reduced fluidic resistance, thus leading to portions of the fluid being shifted away from the primary direction of propagation.

In FIG. 3, the fluidic resistance of the channels is controlled by the geometry of the outer boundaries of each channel. For instance, with respect to each array, the distance between the outer channel wall 305 and the islands progressively increases along the direction of fluid flow, leading to lower fluidic resistance. In contrast, the distance between the wall 307 of the divider 215 and the islands 300 progressively decreases along the length of the array in the direction of fluid flow, leading to increased fluidic resistance. As a result, fluid is shifted through the gaps between islands 300 in the directions indicated by arrows 304. For relatively large particles within the fluids, the particles are also subject to inertial lift forces that push the particles away from the gaps, the portions of fluid extracted through the gaps are substantially particle-free.

During operation of fluid exchanger 108, the filtered fluid sample enters both island arrays closer to the walls 305 of the channels, whereas the buffer fluid stream enters the island arrays closer to the walls 307 of divider 215. On average, both the filtered fluid sample and buffer fluid follow a horizontal trajectory through the fluid exchanger 108. Though the fluid sample has been filtered prior to this stage, it can still contain one or more different sub-populations of particles having different sizes. Depending on the size of the gaps between islands 300 and the flow speed of the fluid sample, larger particles can experience a strong repulsive inertial lift force while flowing alongside the islands 300, which causes those particles to follow a trajectory with a component that leads from the filtered fluid sample stream (closer to walls 305) across fluid streamlines and into to the buffer fluid stream (closer to walls 307). Smaller particles can experience a relatively weaker inertial lift force while flowing alongside the islands 300. As a result, the smaller particles can follow the same average trajectory as the filtered fluid sample and can not be transferred into the buffer fluid stream. At the output of the fluid exchanger 108, the filtered fluid stream will leave the arrays without one or more of the sub-populations of particles (e.g., without the relatively large particles), whereas the buffer fluid stream will have picked up the one or more sub-populations of particles. In some embodiments, one or more of the fluid samples that enter fluid exchange module 108 can come from the particle concentration module 110, described in further detail below.

As indicated above, the inertial lift force is highly size dependent, such that large particles can experience a larger force than small particles. Additionally, the fraction of fluid that is extracted through gaps between islands 300 can be adjusted based on the island design and configuration. Further discussion on the parameters and design principles for such fluid exchangers can be found in U.S. Provisional Application No. 62/074,213, filed Nov. 3, 2014, and U.S. Provisional Application No. 62/074,315, filed Nov. 3, 2014, each of which is incorporated herein by reference in its entirety.

Figure 4:
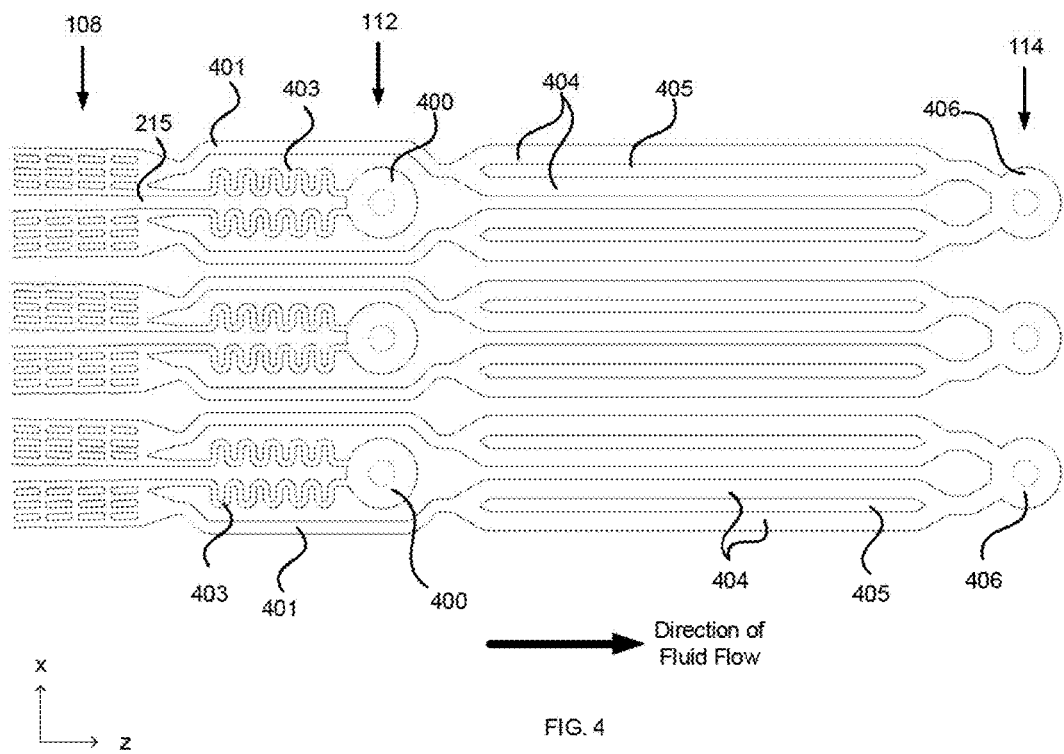
FIG. 4 is a schematic that illustrates a top view of both the product receptacle and the waste receptacle for the fluid exchange module shown in FIG. 3.

Fluid Exchanger Module Product Receptacle and Fluid Exchanger Module Waste Receptacle After passing through the fluid exchanger module 108, the processed fluid sample stream that is depleted of the large particles and the buffer sample stream pass to the fluid exchanger module waste receptacle 114 and the fluid exchanger module product receptacle 112, respectively. FIG. 4 is a schematic that illustrates a top view of both the product receptacle 112 and the waste receptacle 114. The direction of fluid flow is noted at the bottom of the figure. Upon leaving the fluid exchanger module 108, the buffer fluid stream continues to travel close to the walls of divider 215 until it passes into channels 403. In some implementations, the channels 403 include a fluid resistor for adjusting the flow rate of the buffer sample stream. For instance, the channels 403 can have a sinusoidal-like shape that to increase the fluid resistance. Following passage through channels 403, the buffer streams enter into through-holes 400 that fluidly couple the buffer streams to the particle concentration module 110. For instance, the through-holes 400 can be coupled to a connector, such as tubing, that allows the buffer streams to pass into the particle concentration module. Alternatively, the through-holes 400 can be coupled to a manifold that redirect the buffer fluid streams to the particle concentration module. In some implementations, buffer streams pass directly from the fluid exchanger module 108 to the particle concentration module 110 without first propagating through channels and/or through-holes 400.

The processed fluid sample streams (depleted of large particles), in contrast, pass from the fluid exchanger module 108 through microfluidic channels 401 and channels 405 to the fluid exchanger waste receptacle 114. The waste receptacle section 114 can include, for example, through-holes 406 that collect the processed fluid stream. Again, the through-holes can be coupled to tubing or to a manifold that redirects the fluid stream. In some implementations, the waste receptacle section 114 does not include through-holes and instead contains a reservoir to receive the processed fluid sample streams. The number of channels used to couple the fluid exchanger module 108 to the waste receptacle section 114 and to the product receptacle section 112 can be modified from that shown in FIG. 4. For instance, in some implementations, one channel, three channels, four channels or more can be used to couple the processed fluid sample streams from fluid exchanger module 108 to the waste receptacle section 114. Similarly, in some implementations, one channel, three channels, four channels or more can be sued to couple the buffer fluid streams from the fluid exchanger module 108 to the product receptacle section 112.

Particle Concentration Module

As explained above, the buffer fluid stream containing the one or more sub-populations of particles extracted from the sample fluid stream passes from the fluid exchanger product receptacle section 112 to the particle concentration module 110. The particle concentration module 110 is configured and arranged to further enrich the concentration of the sub-population of particles within the buffer stream through a combination of inertial focusing techniques and fluid shifting.

Figure 5:
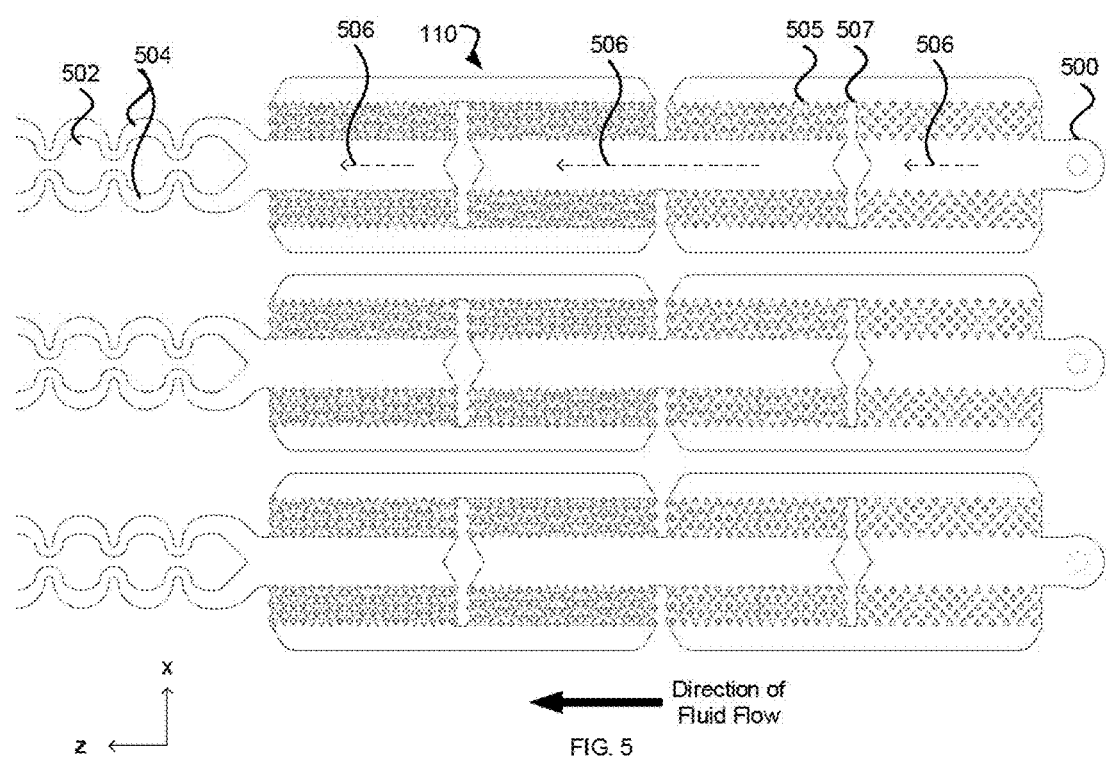
FIG. 5 is a schematic that illustrates a top view of the entrance portion to the particle concentration module of the device shown in FIG. 1.

FIG. 5 is a schematic that illustrates a top view of the entrance portion to the particle concentration module 110 (e.g., corresponding to particle concentration module input section 118 shown in FIG. 1). The general direction of fluid flow is indicated at the bottom of the page. The buffer fluid stream containing the one or more sub-populations of particles enters the particle concentration module 110 at through-holes 500. The through-holes 500 can be fluidly coupled to the through-holes 400 from the product receptacle section 112 using, e.g., tubing or a manifold. Upon entering the particle concentration module 110, the buffer fluid stream passes to one or more filter arrays. The filter arrays can be constructed similar to the filter arrays shown in FIG. 2. For example, the filter arrays can include multiple post structures 505 arranged and configured to filter particles contained in the buffer stream according to the particle size (e.g., average diameter), such that only particles of a pre-defined size or less are able to pass to the next stage of the system. As shown in FIG. 5, the arrays of posts 505 are arranged on either side of the buffer stream flow (indicated by arrows 506). The filter arrays can also include walls/dividers 507 so that the buffer streams 506 are forced around the walls 507 and through the posts 505. The posts 505 of the arrays can be configured and arranged to filter particles of the same size as those previously filtered or particles having a smaller size.

The filter arrays are fluidly coupled to a particle focusing section of the particle concentration module 110. The particle focusing section is configured to pre-focus particles exiting the filter arrays to a desired fluid streamline position before enriching the particle concentration. An advantage of pre-focusing the particles is that, in certain implementations, it reduces the distribution of particles across the channel width to a narrow lateral extent. The focused line of particles then can be repositioned so that the probability of the particles inadvertently entering the wrong channel or being extracted with waste fluid is reduced.

Pre-focusing can be achieved using inertial focusing, where the structure and arrangement of the fluid pathways are designed to generate forces that drive particles within a fluid sample to desired streamlines. The particle focusing section shown in FIG. 5 includes a dividing wall 502 that separates two microfluidic channels 504 fluidly coupled to the output of the filter arrays. Each channel 504 has an undulating pathway defined by the surfaces of the dividing wall 502 and the outer channel walls, where the contour of the dividing wall surfaces match the contour of the outer channel wall it is facing. With the undulating pathways shown in FIG. 5, the microfluidic channels alternate between regions having relatively high curvature and regions having relatively low curvature.

In general, "focusing" particles refers to re-positioning the particles across a lateral extent of the channel and within a width that is less than the channel width. For example, the techniques disclosed herein can localize particles suspended in a fluid within a length of the channel having a width of 1.05, 2, 4, 6, 8, 10, 20, 30, 40, 50, 60, 70, 80, 90, or 100 times the average diameter of the particles. In some implementations, the particles are focused to a streamline of a fluid. In some implementations, a streamline defines a width that is substantially equal to or slightly greater than an average hydraulic diameter of the particle, which can be, but is not limited to, between about 1 µm and about 100 µm.

Further discussion on the parameters and design principles for fabricating inertial focusing structures can be found, for example, in U.S. Pat. No. 8,186,913, U.S. Provisional Application No. 62/074,213, filed Nov. 3, 2014, and U.S. Provisional Application No. 62/074,315, filed Nov. 3, 2014, each of which is incorporated herein by reference in its entirety.

For instance, various channel geometries can require a predetermined particle to volume ratio of the particle to be focused in order to achieve a required interparticle spacing and thereby maintain ordering and focusing of that particle. In particular, the particle to volume ratio of a particle suspended within a fluid can be calculated and adjusted as needed to achieve focusing within certain channel geometries. In general, a maximum particle to volume ratio for a specified particle size and channel geometry can be determined using the formula:

$$\text{MaxVolumeFraction} = 2N\pi\alpha^2/3hw$$

where N is the number of focusing positions in a channel, a is the focused particle diameter, h is the channel height, and w is the channel width. Thus, samples can be diluted or concentrated to attain a predetermined ratio before and/or during introduction of the sample into the system. Particle to volume ratios of a sample within the channels described herein can have any value sufficient to enable ordering and focusing of particles. In general, the particle to volume ratio can be less than about 50%. In other embodiments, particle to volume ratios can be less than about 40%, 30%, 20%, 10%, 8%, or 6%. More particularly, in some embodiments, particle to volume ratios can be in a range of about 0.001% to about 5%, and can preferably be in a range of about 0.01% to about 4%.

In general, there are certain parameters within straight, symmetric, and asymmetric microfluidic channels that lead to optimal ordering and focusing conditions for particles suspended within a sample. These parameters can include, for example, channel geometries, particle size with respect to channel geometries, properties of fluid flow through micro fluidic channels, and forces associated with particles flowing within micro fluidic channels under laminar flow conditions. It is presently believed that the forces acting on the particles can be referred to as inertial forces, however, it is possible that other forces contribute to the focusing and ordering behaviors. Exemplary inertial forces can include, but are not limited to, inertial lift down shear gradients and away from channel walls, Dean drag (viscous drag), pressure drag from Dean flow, and centrifugal forces acting on individual particles. The theory discussed below is meant to be solely descriptive and exemplary and, while the behavior of systems designed using these principles can be predicted using this theory, the theory presented should not be considered as limiting the invention to any of the parameters associated with any of the system embodiments disclosed herein or any particular theory of operation.

In general, inertial lift forces in laminar microfluidic systems, such as those described in the embodiments herein, can act to focus randomly distributed particles continuously and at high rates into a single streamline. Particle geometry dependence can be used to develop systems for high-throughput separations. Channel geometry can be changed to reduce focusing particles from an annulus to four points, to two points, and then to a single point within the channel. Two additional levels of particle ordering can be observed, in particular, longitudinally along the channel length and rotationally (for asymmetric particles). In general, separation, ordering, and focusing is primarily controlled by a ratio of particle size to channel size and the flow characteristics of the system. Advantageously, the focusing is independent of particle density.

Lateral migration of particles in shear flow arises from the presence of inertial lift, attributed mainly to the shear-gradient-induced inertia (lift in an unbounded parabolic flow) that is directed down the shear gradient toward the wall, and the wall induced inertia which pushes particles away from the wall. Particles suspended in fluids are subjected to drag and lift forces that scale independently with the fluid dynamic parameters of the system. Two dimensionless Reynolds numbers can be defined to describe the flow of particles in closed channel systems: the channel Reynolds number (Rc), which describes the unperturbed channel flow, and the particle Reynolds number (Rp), which includes parameters describing both the particle and the channel through which it is translating.

$$Rc \ (U_m D_h)/\nu \text{ and } Rp-Rc \ (\alpha^2/D_h^2)(U m \alpha^2)/(\nu D)$$

Both dimensionless groups depend on the maximum channel velocity, $U_m$, the kinematic viscosity of the fluid, and $\nu=\mu/\rho$ ($\mu$ and $\rho$ being the dynamic viscosity and density of the fluid, respectively), and $D_h$, the hydraulic diameter, defined as $2wh/(w+h)$ (w and h being the width and height of the channel). The particle Reynolds number has an additional dependence on the particle diameter, a. The definition of Reynolds number based on the mean channel velocity can be related to $R_c$ by $R_e = \frac{2}{3}R_c$.

Inertial lift forces dominate particle behavior when the particle Reynolds number is of order 1. Typically, particle flow in microscale channels is dominated by viscous interactions with Rp<<1. In these systems, particles are accelerated to the local fluid velocity because of viscous drag of the fluid over the particle surface. Dilute suspensions of neutrally buoyant particles are not observed to migrate across streamlines, resulting in the same distribution seen at the inlet, along the length, and at the outlet of a channel. As Rp increases, migration across streamlines occurs in macroscale systems. In a cylindrical tube, particles were observed to migrate away from the tube center and walls to form a focused annulus. The theoretical basis for this "tubular pinch" effect is a combination of inertial lift forces acting on particles at high particle Reynolds numbers. The dominant forces on rigid particles are the "wall effect," where an asymmetric wake of a particle near the wall leads to a lift force away from the wall, and the shear-gradient-induced lift force that is directed down the shear gradient and toward the wall.

Channels with curvature create additional drag forces on particles. When introducing curvature into rectangular channels, secondary flows develop perpendicular to the streamwise direction due to the nonuniform inertia of the fluid. In a parabolic velocity profile, faster moving fluid elements within the center of a curving channel can develop a larger inertia than elements near the channel edges. These elements can move toward the channel outer edge, and in order to conserve mass at all points where the fluid is recirculated along the top and bottom of the channel. Two dimensionless numbers can be written to characterize this flow, the Dean number ($D_e$) based on the maximum velocity in the channel, and the curvature ratio ($\delta$). The Dean number, $D_e = Rc(D_h/2r)^{1/2}$ and the curvature ratio, $\delta = D_h/2r$, where r is the average radius of curvature of the channel. For moderate $D_e < 75$ observed in the microfluidic systems described herein, the secondary rotational flow, or Dean flow, consists of only two vortices. The velocity magnitude of the Dean flow scales as $UD \sim \rho D_e^2/(\mu D_h)$ and therefore, Stokes drag on suspended particles due to this secondary flow becomes significant for large $D_e$. In general, the drag due to to Dean flow, or Dean drag ($F_D$) scales as $$F_D \sim (\rho U_m^2 a D_h^2)/r.$$

In short, three flow regimes can be considered: (1) At low fluid velocities, the ratio of lift to drag forces, $R_f$, may be larger than 1 over the majority of the channel cross section; however, the magnitudes of $F_z$ and $F_D$ are too low to create focused streams within the length of channel. (2) At intermediate fluid velocities, $R_f$ may be greater or equal to 1 over a limited region of the channel cross section, and the magnitude of forces is large enough to create focusing to one or more streams. (3) For high fluid velocities, $R_f$ is less than 1 over the entire channel cross section, and Dean drag is dominant, leading to particle mixing.

Figure 6:
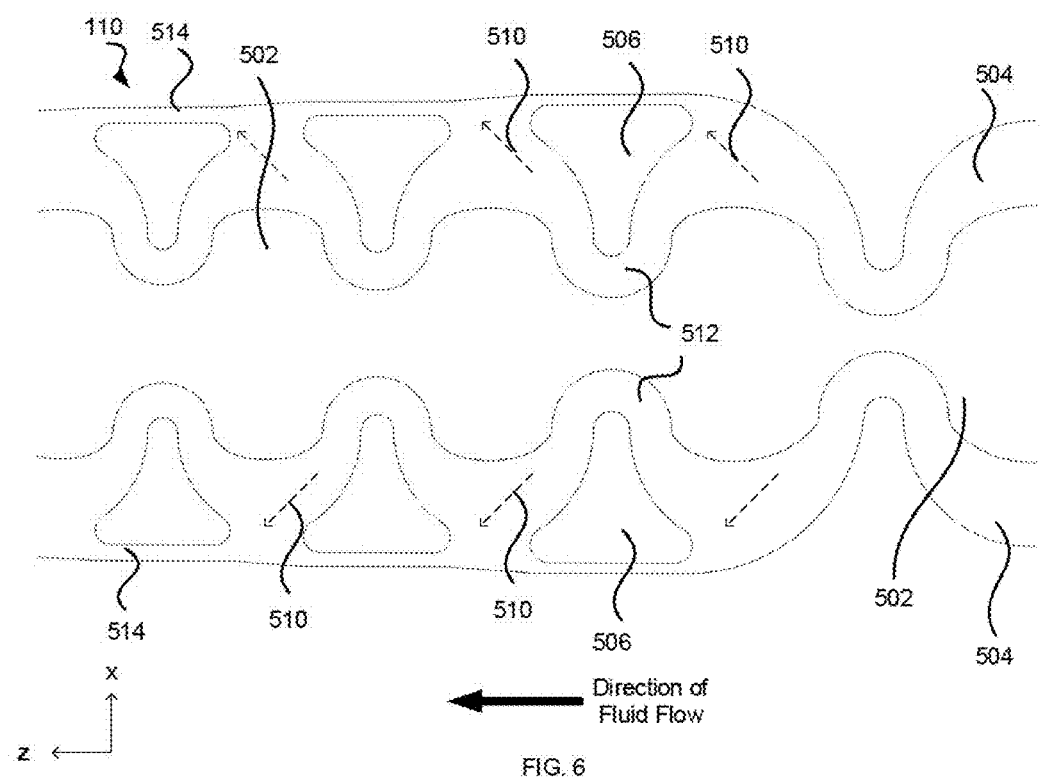
FIG. 6 is a schematic that illustrates a top view of the particle concentration module of the device shown in FIG. 1.

Referring again to device 100, the buffer fluid stream passes from the inertial focusing section of the particle concentration module 110 to microfluidic channels configured to increase the concentration of one or more sub-populations of particles within the buffer stream. FIG. 6 is a schematic that illustrates a top view of the portion of the particle concentration module 110 for enriching particle concentration. The direction of fluid flow through the module 110 is shown at the bottom of the page. In particular, the buffer stream exits the microfluidic channels 504 of the pre-focusing section and passes into microfluidic channels 512 or 514. A first pair of channels 512, 514 remains separated from a second pair of channels 512, 514 by wall 502. Each of channels 512 and 514 are themselves separated from one another by an array of post structures 506. The post structures are spaced apart from one another by gaps through which fluid can be extracted (along, e.g., a direction indicated by arrows 510).

Figure 7:
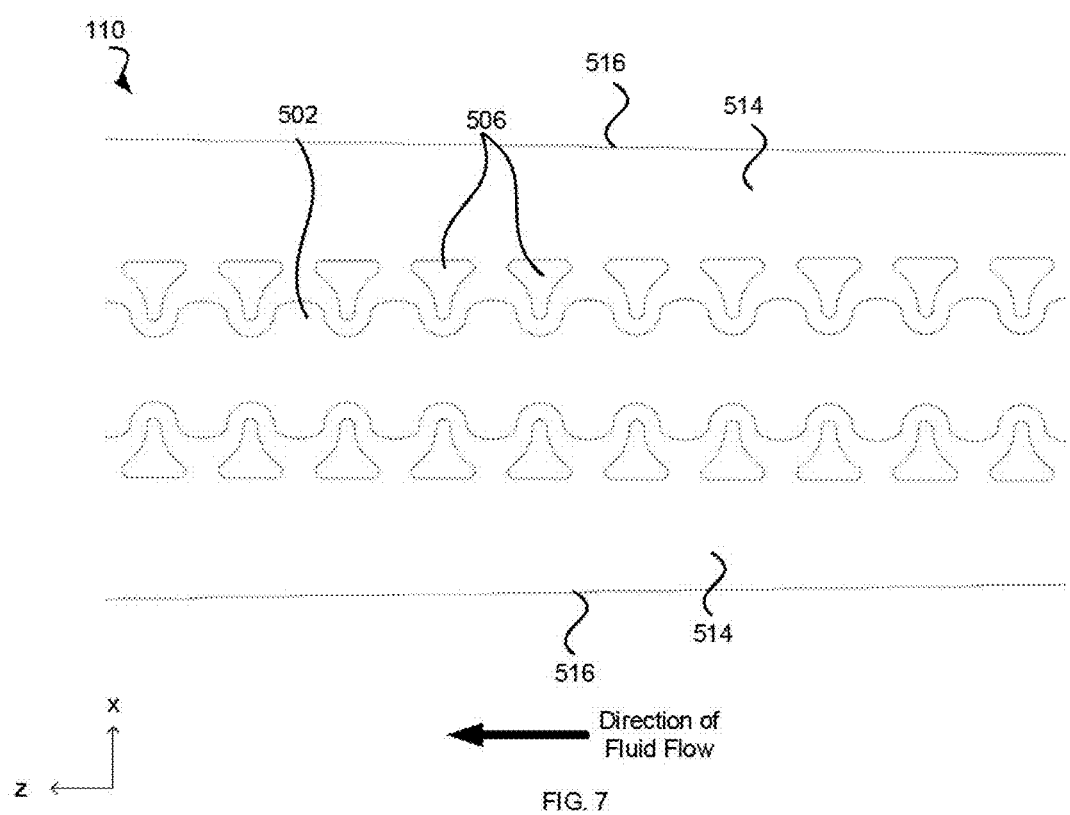
FIG. 7 is a schematic that illustrates a top view of the particle concentration module of the device shown in FIG. 1.

Generally, the pre-focusing positioned the particles within the buffer stream along one or more streamlines that are closer to the surfaces of wall 502 so that, as the buffer stream exits the pre-focuser, the particles are aligned to the channels 512. The design and configuration of the channels 512 are similar to channels 504 in that the pathway is undulating and alternates between areas of relatively high curvature and areas of relatively low curvature. This channel shape again gives rise to inertial forces that focus one or more sub-populations of particles to streamlines within channels 512. At the same time, however, channels 514 are configured to have a decreasing fluidic resistance such that portions of the buffer fluid are repeatedly extracted into channels 514 as indicated by arrows 510, similar to the fluid extraction that takes place in the fluid exchanger module 108. That is, the distance between the outer walls 516 and the island structures 506 progressively increases along the length of the channels 514. For example, FIG. 7 is a schematic that illustrates the walls 516 are oriented at an angle with respect to islands 506, such that the width of channels 514 continues to increase downstream (the distance to the wall from the island structures is much greater further down the channel, as shown in FIG. 7, than near the input, as shown in FIG. 6). Because the inertial focusing drives the particles to streamlines away from the gaps where fluid extraction takes place, the extracted portions of fluid are substantially particle-free. By repetitively removing/siphoning particle-free buffer fluid from the channels 512, the concentration of particles relative to the buffer fluid in channels 512 substantially increases relative to their concentration upon exiting channels 504.

Design parameters that are relevant for establishing the amount of particle-free fluid extracted at each gap between islands 506 and for positioning the focused particles along one or more streamlines include, among others, the lengths of the channels 512, 514, the widths of the channels 512, 514, the spacing between islands 506, and the flow speed of fluid through the particle concentration module 110. For example, the maximum flow rate in which a particle-free layer can form and be extracted through the gaps between islands 506 follows a generally linear relationship with the width of the particle concentration channels (as measured in the x-direction of FIG. 7 between a channel wall 512 and the opposing wall of the divider 502). In another example, the yield of the device 100 can be adversely affected by flow rates through the particle concentration module 110 that are too low (i.e., low Reynolds numbers) such that inertial forces are not large enough to focus particles to streamlines.

Figure 8:
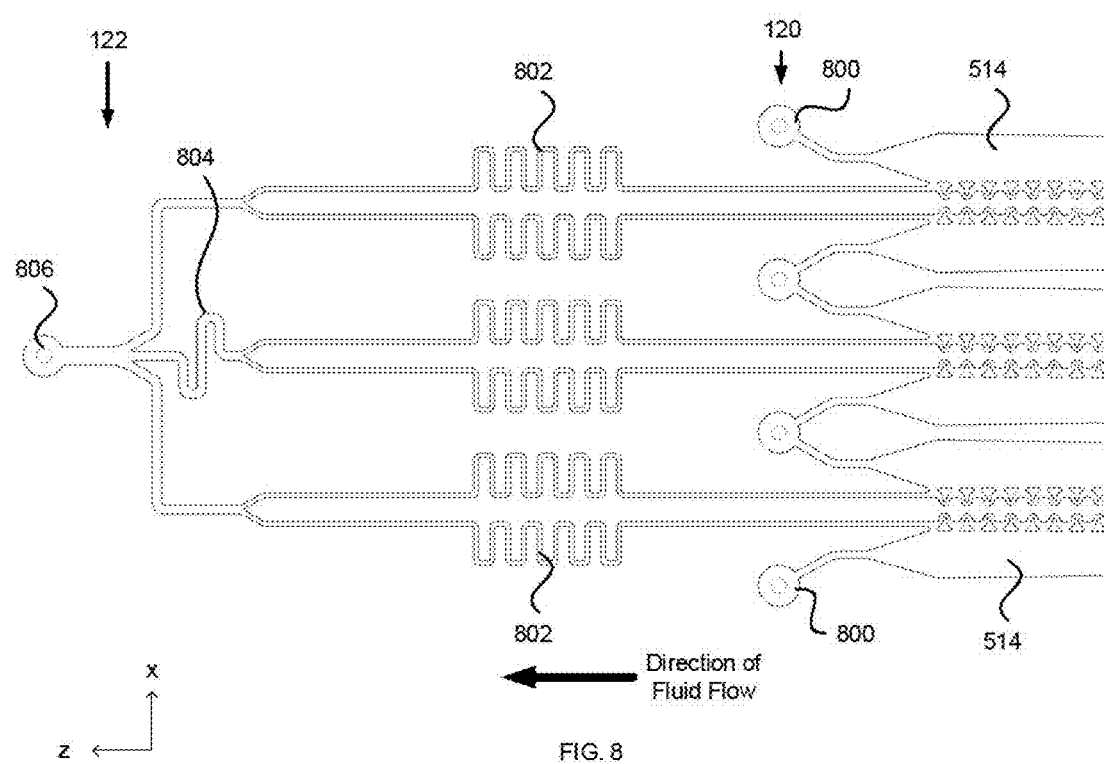
FIG. 8 is a schematic that illustrates a top view of the waste section and product output section for the particle concentration module shown in FIG. 7.

Further discussion on the parameters and design principles for fabricating structures that combine inertial focusing and fluid extraction to enhance particle concentration can be found, for example, in U.S. Provisional Application No. 62/074,213, filed Nov. 3, 2014, and U.S. Provisional Application No. 62/074,315, filed Nov. 3, 2014, each of which is incorporated herein by reference in its entirety. For instance, Particle Concentration Module Waste and Particle Concentration Module Product Output Upon exiting the particle concentration module, the buffer stream containing the enriched population of particles is passed to a product output section 122 where the particles can be collected for further processing and/or analysis. The portions of the particle-free buffer fluid that have been extracted are passed to a waste section 120, where the buffer fluid can be disposed of or further analyzed and/or processed. FIG. 8 is a schematic that illustrates a top view of the waste section 120 and product output section 122. As shown in FIG. 8, channels 514, which include the particle-free buffer solution, are fluidly coupled to the waste section 120. The waste section 120 can include one or more through-holes 800 into which the particle-free buffer solution passes.

The channels containing the particle enriched buffer solution, in contrast, are fluidly coupled to the product output section 122. In the implementation depicted in FIG. 8, the channels coupled to product output 122 can include one or more fluid resistor sections, such as fluid resistors 802 and 804. The fluid resistors 802 and 804 can be configured and arranged to obtain the correct flow rates for the buffer fluid as it passes to the product output 122. For instance, in the present example shown in FIG. 8, the fluid resistors 802 and 804 include sinusoidal-shaped channels that increase the fluid resistance. The center channel that is coupled to through-hole 806 includes the additional fluid resistor 804 to modify the buffer fluid flow rate in that channel so that it matches the flow rate of buffer solution coming from the longer upper and lower channels that are also coupled to the through-hole 806.

By using the particle concentration module 110, it can be possible, in some implementations, to enhance the concentration of particles that have been transferred to a second fluid sample from a first fluid sample by substantial amounts. For example, the concentration can be enhanced between about 5 times and about 100 times the original concentration of the particles prior to entering the particle concentration module including, e.g., about 10 times, about 20 times, about 30 times, about 40 times, about 50 times, about 60 times, about 70 times, about 80 times, or about 90 times the original particle concentration.

In addition, by combining the fluid exchanger module 108 and the particle concentration module 110 in a single microfluidic device, it is possible to extract substantially high yields of desired sub-populations of particles from a fluid sample. For example, in some implementations, the device 100 can be used to obtain particle yields from an initial fluid sample greater than about 70%, greater than about 80%, greater than about 85%, greater than about 90%, greater than about 95%, greater than about 99%, greater than about 99.9%, or greater than 99.99% yield, where yield can be understood to mean the percentage of number of desired particles extracted from the fluid sample relative to the number of desired particles originally contained within the fluid sample when the fluid sample was introduced into the device.

In the examples disclosed above, the fluid exchange module can be used to deplete relatively large particles from a fluid sample and transfer those particles to a second fluid such as a buffer fluid. As a result, the fluid sample that is depleted becomes the waste, whereas the buffer solution becomes the product. It is also possible, in some implementations, to keep the fluid sample that is depleted of the relatively large particles as the product and remove the second fluid to which the relatively large particles have been transferred as the waste. In such cases, the device can be configured to alter (e.g., enrich) the concentration of the fluid sample that is kept as product in the particle concentration module instead of the second fluid sample that contains the transferred particles. For example, the fluid exchange module fractionator can be designed to have a cutoff size for removing white blood cells and red blood cells from a blood sample and then enrich the concentration of the platelets remaining in the blood sample stream.

Fabrication of Microfluidic Devices

A process for fabricating a microfluidic device according to the present disclosure is set forth as follows. A substrate layer is first provided. The substrate layer can include, e.g., glass, plastic or silicon wafer. An optional thin film layer (e.g., $SiO_2$) can be formed on a surface of the substrate layer using, for example, thermal or electron beam deposition. The substrate and optional thin film layer provide a base in which the microfluidic channels depicted throughout FIGS. 2-8 can be formed. The thickness of the substrate can fall within the range of approximately 500 μm to approximately 10 mm. For example, the thickness of the substrate 210 can be 600 μm, 750 μm, 900 μm, 1 mm, 2 mm, 3 mm, 4 mm, 5 mm, 6 mm, 7 mm, 8 mm, or 9 mm. Other thicknesses are possible as well.

The microfluidic channels formed within the substrate include the different fluid flow pathways for the fluid sample and the buffer, such as the straight channels, the filter arrays, the fluidic resistors, the channels within the fluid exchanger module, and the channels within the particle concentration module. The microfluidic channels can be formed, in some implementations, by depositing a polymer (e.g., polydimethylsiloxane (PDMS), polymethylmethacrylate (PMMA), polycarbonate (PC), or cyclo olefin polymer (COP)) in a mold that defines the fluidic channel regions. The polymer, once cured, then can be transferred and bonded to a surface of a support layer. For example, PDMS can be first poured into a mold (e.g., an SU-8 mold fabricated with two step photolithography (MicroChem)) that defines the microfluidic network of channels. The PDMS then is cured (e.g., heating at 65° C. for about 3 hours). Prior to transferring the solid PDMS structure to the support layer, the surface of the substrate layer is treated with $O_2$ plasma to enhance bonding. Alternatively, if the microfluidic channels are fabricated in other substrate materials, such as a glass or silicon wafer, the channels can be formed using standard semiconductor photolithography processing to define the channel regions in combination with wet and/or dry etching techniques to fabricate the channels.

After forming the microfluidic channels within the substrate, the substrate, also referred to as the "fluidic layer," can be covered with a lid layer. The lid layer seals the fluidic layer microchannels (i.e., forms the "ceiling" of each channel) and is aligned and bonded to the fluidic layer. Bonding can be achieved using, e.g., an adhesive. The lid layer can include through-holes that are aligned with the through-holes formed in the fluidic layer, so as to allow fluids to be introduced and withdrawn from the device. Alternatively, or in addition, the through-holes can be formed in the fluid layer such that, in some implementations, the lid layer is not necessary. In some implementations, a third interface layer couples to the surface of the lid layer. The interface layer can include a manifold that enables macro-scale connections to the device.

Figure 9:
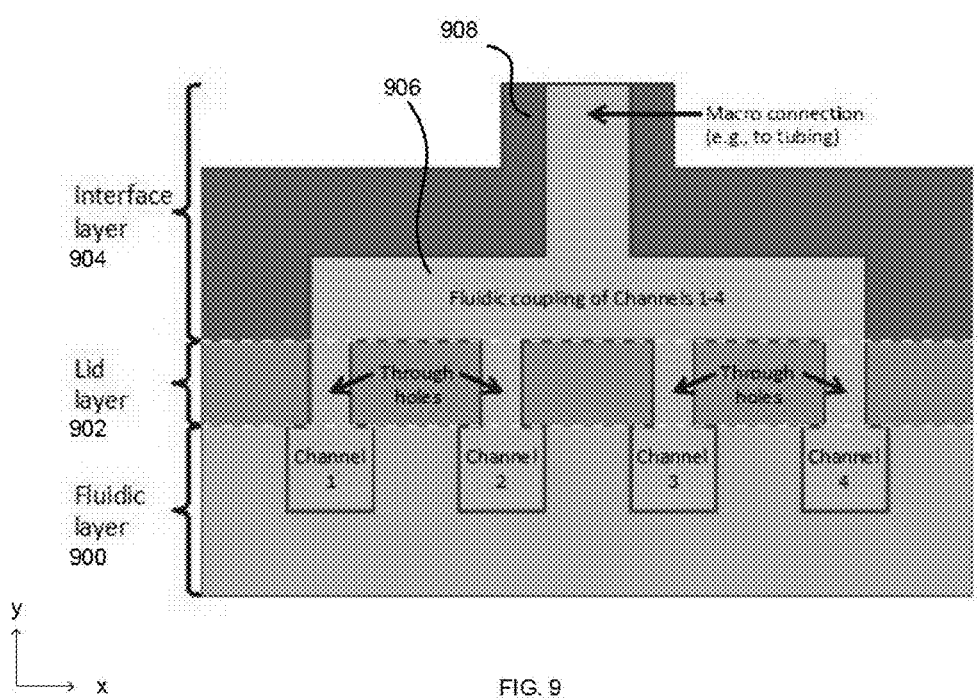
FIG. 9 is a schematic that illustrates a generalized cross-section of a microfluidic device according to the present disclosure.

FIG. 9 is a schematic that illustrates a cross-section of a device, such as device 100, according to the present disclosure. The view shown in FIG. 9 is a generalized cross-section and does not correspond to any one particular location in the device 100. As shown in the cross-section, the device 100 includes a fluidic layer 900, in which the microfluidic channels are formed. A top surface of fluidic layer 900 is bonded to the lid layer 902 (not shown in FIG. 1). The through-holes of the fluidic layer 900 can be aligned with the through-holes in the lid layer. The interface layer 904 (not shown in FIG. 1) includes one or more manifold sections 906 for establishing a common macro-connection (e.g., to tubing) to multiple through-holes of the device 100. For instance, the interface layer 904 can include a first manifold section for providing a single coupling connection to the multiple through-holes 200 (see FIG. 2) and another manifold section for providing a single coupling connection from the multiple through-holes 800 (see FIG. 8). The interface layer 904 can be laser welded to the lid layer 902.

In some implementations, a manifold of the interface layer 904 includes a port 908 for enabling the macro-connection.

Additional information about microfluidic channel networks and their fabrication can be found, for example, in U.S. Patent App. Publication No. 2011/0091987, U.S. Pat. Nos. 8,021,614, and 8,186,913, each of which is disclosed herein by reference in its entirety.

Microfluidic Device Dimensions

For generally spherical particles being transported through a microfluidic device, the depth (e.g., as measured into/out of the page for FIGS. 2-8) and width (e.g., as measured along the x-direction in FIGS. 2-8) of the microfluidic channels can be, for example, in the range of about 2 times to about 50 times the diameter of the type of particle for which the device 100 is designed to enrich. With respect to the island structures 300 that form the gaps through which fluid is extracted in the fluid exchanger module 108 or the island structures 506 that form the gaps through which fluid is extracted in the particle concentration module 110, the width of the structures can be, e.g., up to about 10 times the width of an adjacent microfluidic channel, whereas the length of those structures can be between about 0.25 times the adjacent channel width up to about 50 times the adjacent channel width.

In some implementations, the length of the island structures 300 (as measured generally along the z-direction in FIG. 3) can be between, e.g., about 10 µm to about 5 mm long, including about 100 µm long, about 250 µm long, about 500 µm long, about 750 µm long, or about 1 mm long. In some implementations, the width of the structures 300 (as measured generally along the x-direction in FIG. 3) can be between, e.g., about 1 µm wide to about 1 mm wide, including about 10 µm wide, about 50 µm wide, about 100 µm wide, about 250 µm wide, about 500 µm wide, or about 750 µm wide. In some implementations, the distance between adjacent islands 300 (as measured generally along the z-direction in FIG. 3) can be between, e.g., about 1 µm to about 1 mm, including about 10 µm, about 50 µm, about 100 µm, about 250 µm, about 500 µm, or about 750 µm. In some implementations, the distance between the outermost islands 300 of the arrays and the microfluidic channel walls (e.g., walls 305 or 307) can vary between about 1 µm to about 500 µm, including, for example, about 10 µm, about 20 pm, about 30 µm, about 40 µm, about 50 µm, about 60 µm, about 70 pm, about 80 µm, about 90 µm, about 100 µm, about 150 µm, about 200 µm, about 250 µm, about 300 µm, about 350 µm, about 400 µm, or about 450 µm. In some implementations, the length of the fluidic exchanger module 108 (as measured generally along the z-direction from one end of the array of islands 300 to the other end of the array of islands 300) can be between, e.g., about 10 mm to about 100 mm, including about 20 mm, about 30 mm, about 40 mm, about 50 mm, about 60 mm, about 70 mm, about 80 mm, or about 90 mm.

In contrast to the island structures 300, the island structures of the particle concentration module 110 have a generally triangular prism shape with a maximum width generally corresponding to one base of the triangular face. In some implementations, the maximum length of the island structures 506 can be between, e.g., about 10 µm to about 5 mm long, including about 100 µm long, about 250 µm long, about 500 µm long, about 750 µm long, or about 1 mm long. In some implementations, the distance between adjacent islands 506 (as measured generally along the z-direction in FIG. 7) can be between, e.g., about 1 µm to about 1 mm, including about 10 µm, about 50 µm, about 100 µm, about 250 µm, about 500 µm, or about 750 µm. In some implementations, the distance between the outermost islands 506 of the arrays and the microfluidic channel walls (e.g., walls 516 or walls of divider 502) can vary between about 1 µm to about 500 µm, including, for example, about 10 µm, about 20 pm, about 30 µm, about 40 µm, about 50 µm, about 60 µm, about 70 µm, about 80 µm, about 90 µm, about 100 µm, about 150 µm, about 200 µm, about 250 µm, about 300 µm, about 350 µm, about 400 µm, or about 450 µm. In some implementations, the length of the particle concentration module 110 (as measured generally along the z-direction from one end of the array of islands 506 to the other end of the array of islands 506) can be between, e.g., about 10 mm to about 100 mm, including about 20 mm, about 30 mm, about 40 mm, about 50 mm, about 60 mm, about 70 mm, about 80 mm, or about 90 mm.

As an example, for a generally spherical particle having a diameter of about 8 microns, a microfluidic device having two microfluidic channels separated by an array of rigid structures similar to the configuration shown in FIG. 1 can have the following parameters: each microfluidic channel can have a depth about 52 µm, each microfluidic channel can have a range of widths between about 10 µm to about 5000 µm, each island structure can have a width of about 50 µm, each island structure can have a length of about 200 µm.

Applications

The new microfluidic techniques and devices described herein can be used in various different applications. For example, the techniques and devices disclosed herein can be used to isolate and enrich the concentration of cells or other particles from a fluid sample. Such cells or particles can include, e.g., blood cells in general as well as fetal blood cells in maternal blood, bone marrow cells, and circulating tumor cells (CTCs), sperm, eggs, bacteria, fungi, virus, algae, any prokaryotic or eukaryotic cells, organelles, exosomes, droplets, bubbles, pollutants, precipitates, organic and inorganic particles, magnetic beads, and/or magnetically labeled analytes). Alternatively, or in addition, the techniques and devices disclosed herein can be used to extract purified fluid samples, from which particles and/or cells have been extracted. Such fluids can include, e.g., blood, aqueous solutions, oils, or gases. Examples of specific applications are set forth below.

Centrifugation Replacement

The combined fluid exchanger and particle concentration device described herein can be used as a replacement for centrifugation. In general, centrifugation is understood to include the concentrating of sub-components within a fluid through the application of centrifugal forces to the fluid. Typically, this process requires devices that have moving parts, which are prone to wear and breakage. Moreover, the moving parts require complex and costly fabrication processes. Another problem with centrifugation is that it is a process typically applied in a closed system, i.e., centrifugation requires manually transferring samples to and from a centrifuge.

In contrast, the presently disclosed device is capable of substantially increasing the concentration of fluid components using relatively simple micro-structures without the need for moving parts. The techniques can be implemented as part of a single open microfluidic system, such that fluid samples can be transferred between the fluid exchanger module and the particle concentration module, among other sections of the device without manual interference. Additionally, the device described herein can be used for applications requiring large throughput (i.e., volume rate of fluid that can be processed). For example, the devices disclosed herein can be configured to enable up to 10, 25, 50, 75, 100, 250, 500, 1000, 5000, or 10000 µl/min of fluid flow. Other flow rates are also possible. Varying the channel sizes can alter the maximum volumetric flow rate of which the device is capable. Furthermore, because the channels in the fluid exchanger module and the particle concentration module are multiplexed (i.e., multiple copies of the fluid exchanger and particle concentration structures are used in parallel), even higher rates of flow can be achieved. Thus, in certain implementations, the device and techniques disclosed herein can provide substantial cost and time saving advantages over traditional centrifugation processes. Examples of applications where a microfluidic replacement for a centrifuge device can be useful include bone marrow and urine analysis.

Detecting Infectious Agents

In addition, the device and techniques disclosed herein can be used as part of a research platform to study analytes of interest (e.g., proteins, cells, bacteria, pathogens, and DNA) or as part of a diagnostic assay for diagnosing potential disease states or infectious agents in a patient. By extracting, focusing and enriching particle concentration, the microfluidic device described herein can be used to measure many different biological targets, including small molecules, proteins, nucleic acids, pathogens, and cancer cells. Further examples are described below.

Rare Cell Detection

The microfluidic device and methods described herein can be used to detect rare cells, such as circulating tumor cells (CTC) in a blood sample or fetal cells in blood samples of pregnant females. For example, the concentration of primary tumor cells or CTCs can be enhanced in a blood sample for rapid and comprehensive profiling of cancers. Thus, the microfluidic device can be used as a powerful diagnostic and prognostic tool. The targeted and detected cells could be cancer cells, stem cells, immune cells, white blood cells or other cells including, for example, circulating endothelial cells (using an antibody to an epithelial cell surface marker, e.g., the Epithelial Cell Adhesion Molecule (EpCAM)), or circulating tumor cells (using an antibody to a cancer cell surface marker, e.g., the Melanoma Cell Adhesion molecule (CD146)). The systems and methods also can be used to detect small molecules, proteins, nucleic acids, or pathogens.

Isolation and Concentration of Nucleated Cells

The microfluidic device and techniques disclosed herein can be used to isolate and concentrate nucleated cells (e.g., white blood cells) from complex input fluids, such as blood and bone marrow. For instance, the device can be used to isolate neutrophils from blood for radiolabeling and subsequent injection and nuclear imaging ("leuko-imaging") and/or for enriching progenitor cells from bone marrow aspirate for subsequent injection into orthopedic injury sites.

Fluid Exchange

The microfluidic device and methods described herein can be used to shift cells from one carrier fluid to another carrier fluid. For example, the particle shifting techniques disclosed could be used to shift cells into or out of a fluid stream containing reagents, such as drugs, antibodies, cellular stains, magnetic beads, cryoprotectants, lysing reagents, and/or other other analytes.

A single particle shifting region could contain many parallel fluid streams (from many inlets) through which a shifted cell would pass. For example, white blood cells could be shifted from a blood stream into a stream containing staining reagents and then into a buffer stream.

In bioprocessing and related fields, the devices and techniques described can be used to enable sterile, continuous transfer of cells from old media (containing waste products) into fresh growth media. Similarly, extracellular fluids and cellular products (e.g., antibodies, proteins, sugars, lipids, biopharmaceuticals, alcohols, and various chemicals) can be extracted from a bioreactor in a sterile, continuous manner while cells are retained within the bioreactor.

Separating and Analyzing Cells

The microfluidic device and methods described herein can be used to fractionate cells based on biophysical properties, such as size. For example, the device and methods can be used to fractionate blood into separate platelet, red blood cell, and leukocyte streams. Similarly, the device and methods can be used to fractionate leukocytes into its separate lymphocyte, monocyte, and granulocyte streams.

The streams of fractionated cells can be isolated by routing them into separate fluid outlets. Alternatively, the streams of cells can be detected and analyzed in real-time (e.g., using optical techniques) to determine the number of cells in each stream or properties, such as size or granularity, of the cells in each stream.

Techniques can be used to alter cells or their carrier fluid before or during sorting to facilitate their fractionation and/or analysis. For example, large beads can be bound to a specific cell type increase the effective size of that cell type. Controlled cell aggregation can also be used to increase the effective size of cells. The temperature, density, viscosity, elasticity, pH, osmotic, and other properties of the fluid can be changed to either directly affect the sorting process (e.g., inertial effects are viscosity dependent) or indirectly affect the sorting process by altering the properties of cells (e.g., osmotic swelling or shrinking).

Fluid Sterilization and Cleansing

The microfluidic device microfluidic device and methods described herein can be used to remove pathogens, pollutants, and other particular contaminants from fluids. By shifting contaminants across fluid streamlines, contaminants can be removed from a fluid sample and collected as a separate waste stream.

Harvesting Algae for Biofuels

Harvesting algae from growth media is a major expense in the production of biofuels because algae grow in very dilute suspensions at near neutral buoyancy, making efficient extraction and concentration of algal biomass difficult. The microfluidic device and methods described herein can provide an efficient means of harvesting algae that does not depend on either density or filtration. The devices and techniques described enable the algae in a growth tank to be extracted from the growth media and concentrated to a high volume density. This could be done either as a single step or as part of a continuous process. Additionally, because the devices described herein can sort cells in a size-dependent manner, they can be designed to sort and concentrate only the larger algae that have reached maturity, returning smaller, immature algae to the tank.

EXAMPLES

The invention is further described in the following examples, which do not limit the scope of the invention described in the claims.

Device Fabrication

Various experiments were performed to analyze the behavior of a microfluidic device that combines a fluid exchanger module with a particle concentration module, in which the architecture of the device was designed to follow the structure and arrangement of the components illustrated in FIGS. 1-8. The device used in those experiments were designed and fabricated as follows.

Figure 10:
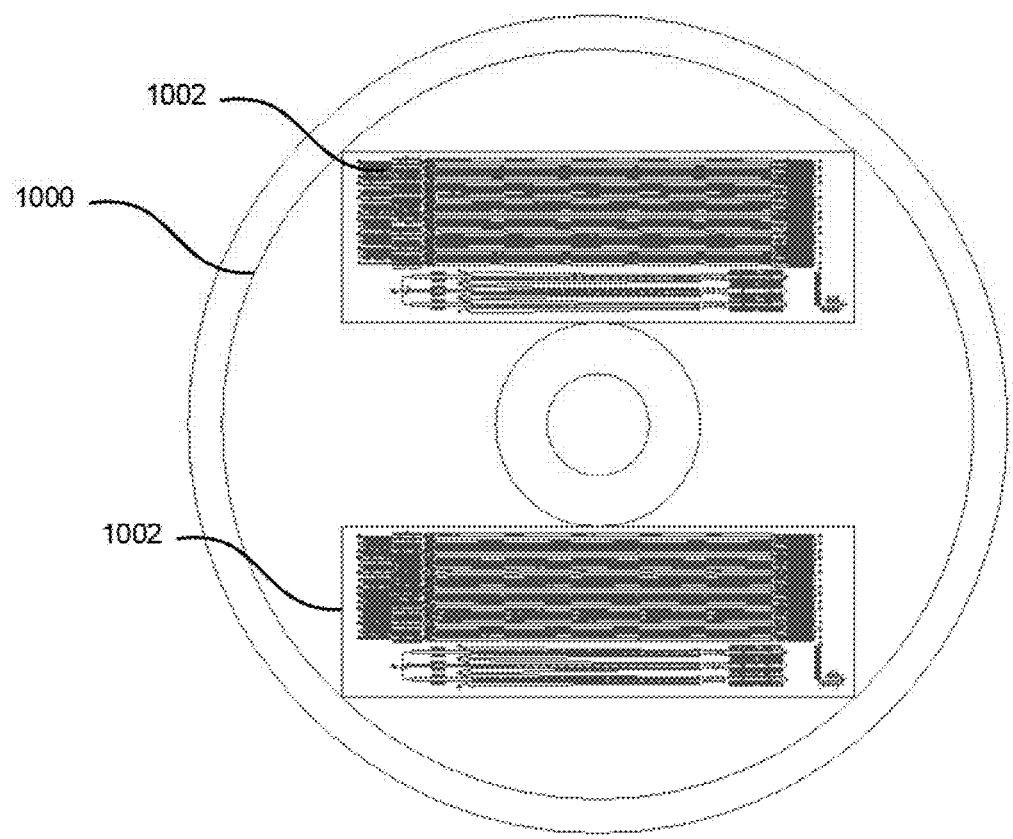
FIG. 10 is a schematic that illustrates a top view of a microfluidic chip that includes the device according to the present disclosure.

FIG. 10 is a schematic that illustrates a top view of a microfluidic chip that includes the device according to the present disclosure. As shown in FIG. 10, a substrate 1000, which is a plastic disc (similar in shape to a DVD or CD), was fabricated to include two copies of the microfluidic device 1002. The designs of the devices 1002 are similar to the architecture illustrated in FIGS. 1-8. The channels of the devices 1002 were formed using injection molding into the plastic disc substrate. The disc is therefore an example of the fluidic layer 900 shown in FIG. 9. Each device 1002 is shown in FIG. 10 surrounded by a rectangular box outline. This outline is not formed in the actual device and is instead included in FIG. 10 to illustrate that the general footprint of each device 1002 fits within a microscope slide area (e.g., about 75 mm×25 mm).

Figure 11:
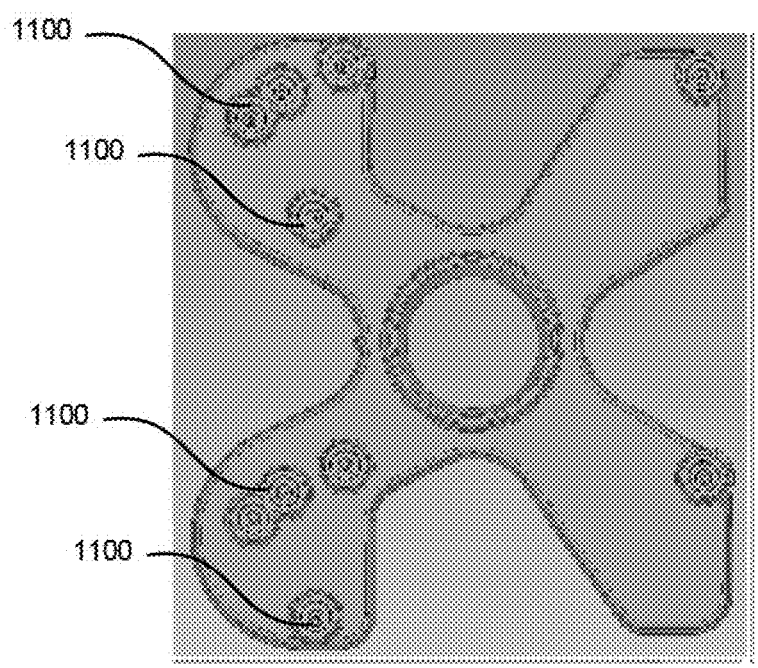
FIG. 11 is a schematic that illustrates a top view of an interface layer that is laser welded to the substrate containing microfluidic devices according to the present disclosure.

A lid layer was thermally bonded to the surface of the disc, followed by laser welding of the interface layer that serves as the macro-micro interface to the through-holes of the devices 1002. FIG. 11 is a schematic that illustrates a top view of an interface layer that is laser welded to the substrate containing the microfluidic devices 1002. The interface layer included a series of openings 1100 that are configured to couple to tubing and, when the interface layer was bonded to the substrate, were situated over corresponding through-holes for introducing fluid samples or withdrawing fluid samples from the devices 1002.

The depths of the microfluidic channels fabricated in the devices 1002 were all approximately 52 μm. The fluid exchanger module of each device 1002 included 30 arrays, arranged as 15 duplexes (for example, the structure shown in FIG. 3 corresponds to two separate arrays or 1 duplex, in which each array includes three rows of islands 300). For the manufactured device, each array included 3 rows of island structures (e.g., island structures 300). The particle concentration module of each device 1002 includes 6 arrays, arranged as 3 duplexes (for example, the structure shown in FIG. 7 corresponds to two arrays or a single duplex).

Cell Extraction and Enrichment

Following fabrication, the devices 1002 as manufactured were used to carry out an experiment in which whole blood was loaded into the device to extract and enrich a concentration of neutrophils.

The blood volume loaded in all experimental runs was 50 mL. It was diluted 1:1 with 50 mL of buffer (1× PBS with 1% Pluronic F-127), bringing the total sample volume to 100 mL.

The median volume processed, calculated from a hematocrit of the input sample and the Fluid Exchanger waste, was about 87 mL (87%). The ~13 mL (13%) loss can have been due to dead volume losses in the sample container, syringes, tubing, and fittings. The diluted blood sample thus corresponds to the fluid sample as described herein. A second fluid sample into which cells from the diluted blood sample would be transferred and enriched included a buffer fluid sample (1× PBS with 1% Pluronic F-127). The flow rate into the devices 1002 for the diluted blood sample was about 1.79 mL/min. the flow rate into the devices for the buffer sample was about 8.17 mL/min. The flow rate of the product (the buffer containing the enriched cells from the blood sample) out of the devices 1002 was about 90 μL/min. The waste flow rate out of the devices 1002 was about 9.87 mL/min. The volume reduction factor (input volume/product volume) of the fluid exchanger module of each device was determined to be about 0.62×. The volume reduction factor of the particle concentration module of each device was determined to be about 32×.

For the purposes of evaluating the experiments, we defined the following parameters: EP corresponds to the number of white blood cells (WBCs) output from the Fluid Exchanger as product, EW corresponds to the number of WBCs output from the Fluid Exchanger as waste, EO corresponds to the total number of WBCs output from the Fluid Exchanger, CP corresponds to the number of WBCs output from the Particle Concentration module as product, CW corresponds to the number of WBCs output from the Particle Concentration module as waste, and CO corresponds to the total number of WBCs output from the Particle Concentration module. Using the foregoing parameters, the following relationships hold true: EP=CO=CP+CW; EO=EP+EW=CP+CW+EW. Accordingly, for the fluid exchanger module, the relative yield can be expressed as EP/EO=(CP+CW)/(CP+CW+EW), and for the particle concentration module, the relative yield can be expressed as CP/CO=CP/(CP+CW).

Figure 12A:
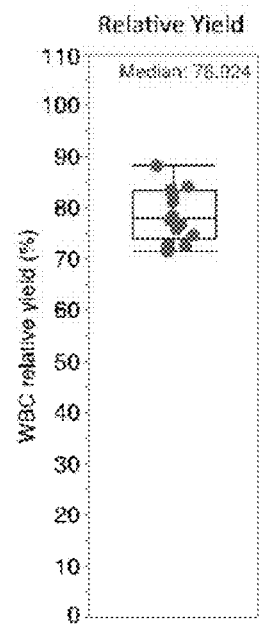
FIG. 12 is a series (FIGS. 12A, 12B) of plots of white blood cell relative yield distribution and white blood cell absolute yield distribution for different experimental runs of the microfluidic device according to the present disclosure.
Figure 12B:
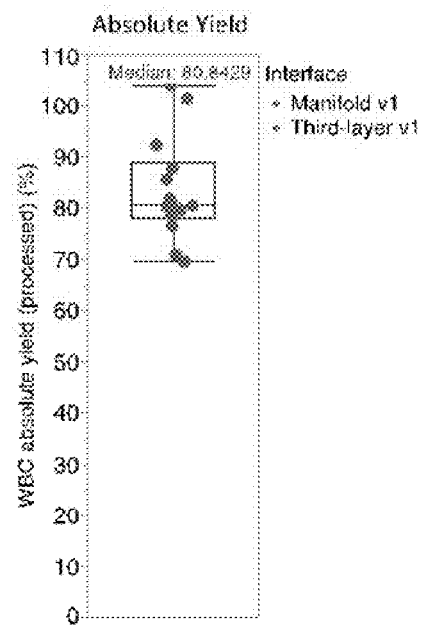
Figures 13A, 13B:
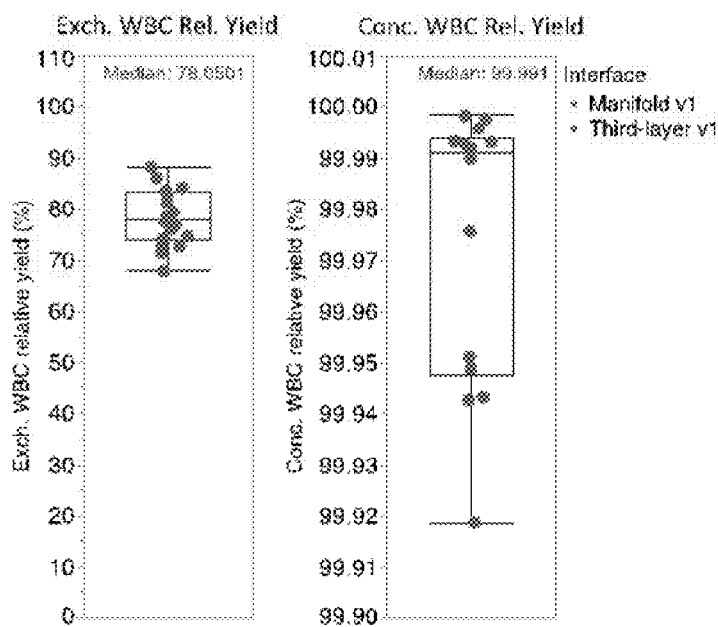
FIG. 13 is a series (FIGS. 13A, 13B) of plots of white blood cell relative yield following the fluid exchanger module (the "fractionator") and white blood cell relative yield following the particle concentration module for different experimental runs of the microfluidic device according to the present disclosure.

The median relative yield of white blood cells (WBCs) after the fluid exchanger module was about 78%, and the median absolute yield (calculated based on the processed volume) was a very similar 81%. FIG. 12 illustrates plots of white blood cell relative yield distribution (FIG. 12A) and white blood cell absolute yield distribution (FIG. 12B) for the different experimental runs. The median relative yield after the particle concentration module stage was about 100%. That is, essentially all loss of cells occurred in the Fluid Exchanger module stage. FIG. 13 illustrates plots of white blood cell relative yield (FIG. 13A) following the fluid exchanger module (the "fractionator") and white blood cell relative yield (FIG. 13B) following the particle concentration module for the different experimental runs.

Figure 14A:
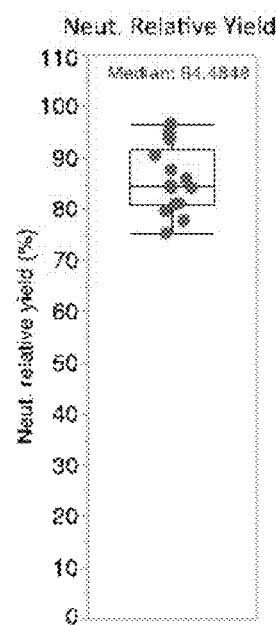
FIG. 14 is a series (FIGS. 14A, 14B) of plots of the relative neutrophil yield and the absolute neutrophil yield from for different experimental runs of the microfluidic device according to the present disclosure.
Figure 14B:
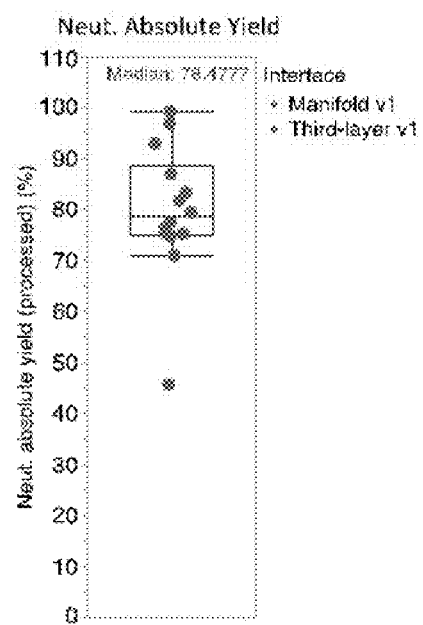

Several approaches can be used to assess the yield of WBC subpopulations. Taking neutrophils as an example, as they can be understood to be an important subpopulation for the leuko-imaging application, the neutrophil relative yield can be calculated as Neutrophil relative yield=WBC relative yield×
(Product neutrophil fraction/Sample neutrophil fraction)

where product neutrophil fraction is the fraction of all WBCs in the product that are neutrophils and sample neutrophil fraction is the fraction of all WBCs in the blood sample that are neutrophils. Thus, the neutrophil relative yield can be expressed as essentially the overall WBC relative yield adjusted based on the relative enrichment of the neutrophil subpopulation. The median neutrophil relative yield is 84%, significantly higher than the median WBC relative yield. The second approach is the neutrophil absolute yield. This is calculated as the total number of neutrophils in the product divided by the total number of neutrophils processed in the sample. The median neutrophil absolute yield is 78%. FIG. 14 illustrates plots of the relative neutrophil yield (FIG. 14A) and the absolute neutrophil yield (FIG. 14B) from the devices 1002 for the different experimental runs.

It should be noted that, with neutrophil relative and absolute yield calculations, these values depend on hematology analyzer analysis of the product obtained from the output of the device, a cell solution whose composition is very different from the composition the analyzer is designed to work with (that of whole blood). As such, the hematology analyzer reports of the concentration and frequency of WBC subpopulations can not be particularly accurate.

Figure 15:
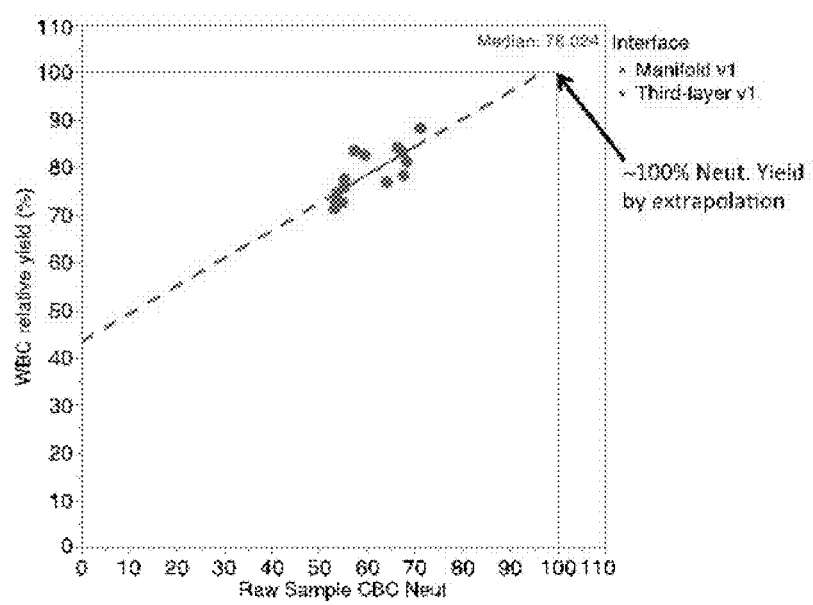
FIG. 15 illustrates a plot of white blood cell (WBC) relative yield versus sample neutrophil fraction for the different experimental runs of the microfluidic device according to the present disclosure.

A third method of assessing the neutrophil yield does not suffer from this limitation, but it does depend on collecting a significant body of data and only provides an estimate of neutrophil yield across many samples, not on a sample-by-sample basis. In this method, the sample neutrophil fraction was plotted against the relative yield for each fraction, and a best-fit line is found to relate the quantities. The best-fit line can be extended to the hypothetical case of a sample with 100% neutrophil fraction. In this case, the WBC relative yield and the neutrophil relative are equivalent. For this dataset, the slope of the best-fit line is positive: the higher the neutrophil content in the sample, the higher the overall WBC yield. This strongly suggests that the devices 1002 enrich for neutrophils, consistent with what one would expect given the larger size of neutrophils. Moreover, using the extrapolation method described suggests that the neutrophil yield is in the range of 100%. FIG. 15 illustrates a plot of WBC relative yield versus sample neutrophil fraction for the different experimental runs and includes the best-fit line described above.

The WBC purity was calculated as the total number of WBCs in the product divided by the total number of cells in the product (WBCs, RBCs, and platelets). The overall median purity was about 97%. Even in the cases where buffer inlets might have been blocked (causing RBC carry-over), the purity was typically between about 70-90%. However, runs that were not subject to either blocked buffer ports or non-uniform injection had a WBC purity of about 99%. Thus, with process improvements one would expect the median WBC to trend toward about 99%.

Figure 16:
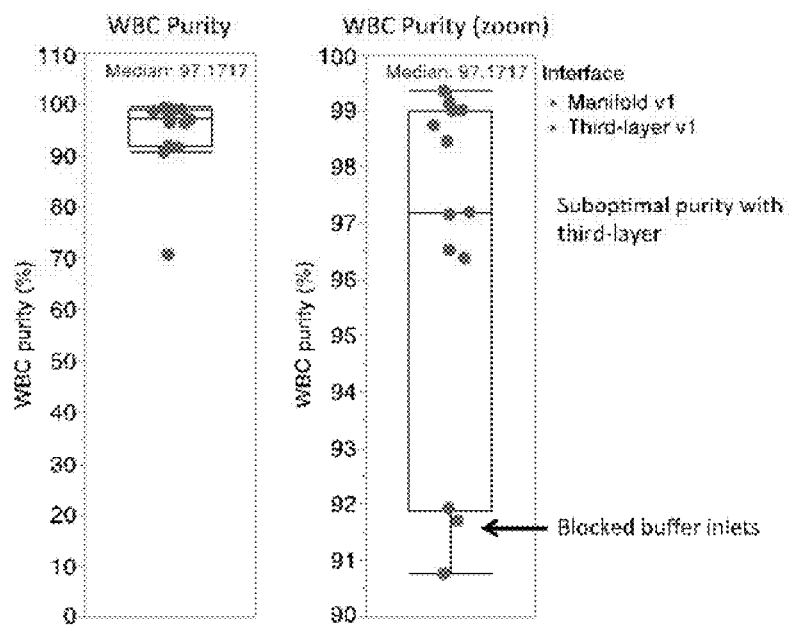
FIG. 16 illustrates plots of red blood cell (RBC) and platelet depletion data

The purity data is closely related to the RBC and platelet depletion data as shown in FIG. 16. The median RBC depletion was 4.8 log and the median platelet depletion was 3.7 log. The depletion of both cell types was generally quite good, the exception being in cases of a blocked buffer port or non-uniform injection.

Other Embodiments

It is to be understood that while the invention has been described in conjunction with the detailed description thereof, the foregoing description is intended to illustrate and not limit the scope of the invention, which is defined by the scope of the appended claims.

What is claimed is:

1. A microfluidic device comprising:
a fluid exchange module, the fluid exchange module comprising a corresponding first microfluidic channel and a first array of island structures in the first microfluidic channel, the first array of island structures being arranged in one or more rows that extend along a longitudinal direction of the first microfluidic channel, each island structure in a row being spaced apart from an adjacent island structure in the row to form an opening,
wherein the first array of island structures in the fluid exchange module is configured and arranged to shift portions of fluid through the opening between adjacent island structures within a row to a first side of the first array, leaving a remaining portion of the fluid on a second opposite side of the first array,
wherein the fluid exchange module further comprises a first fluid exchange output fluidly coupled to the first side of the first array and a second fluid exchange output fluidly coupled to the second opposite side of the first array; and a particle concentration module, the particle concentration module comprising a corresponding second microfluidic channel and a second array of island structures, each island structure in the second array of island structures being spaced apart from an adjacent island structure in the second array of island structures to form an opening,
wherein the second array of island structures in each particle concentration module is configured and arranged to shift portions of fluid through the openings between adjacent island structures in the second array of island structures toward a first side of the second array of island structures, and wherein a shape of the second microfluidic channel is configured to give rise to inertial forces that focus particles contained within the fluid along one or more streamlines on a second opposite side of the second array of island structures, and
wherein the particle concentration module further comprises a first concentration module output fluidly coupled to the second opposite side of the second array of island structures.

2. The microfluidic device of claim 1, wherein the first fluid exchange output of the fluid exchange module is fluidly coupled to an input of the second microfluidic channel of the particle concentration module.

3. The microfluidic device of claim 1, wherein the second fluid exchange output of the fluid exchange module is fluidly coupled to an input of the second microfluidic channel of the particle concentration module.

4. The microfluidic device of claim 2,
comprising a first fluid sample input port and a second fluid sample input port,
wherein the fluid exchange module is arranged to receive in the first microfluidic channel a first fluid sample from the first fluid sample input port and a second fluid sample from the second fluid sample input port.

5. The microfluidic device of claim 3,
comprising a first fluid sample input port and a second fluid sample input port,
wherein the fluid exchange module is arranged to receive in the first microfluidic channel a first fluid sample from the first fluid sample input port and a second fluid sample from the second fluid sample input port.

6. The microfluidic device of claim 1, wherein the first concentration module output of the particle concentration module is fluidly coupled to an input of the first microfluidic channel of the fluid exchange module.

7. The microfluidic device of claim 6, comprising a first fluid sample input port and a second fluid sample input port, wherein the particle concentration module is arranged to receive in the second microfluidic channel a first fluid sample from the first fluid sample input port, and wherein the fluid exchange module is arranged to receive in the first microfluidic channel a second fluid sample from the second fluid sample input port.

8. A method of extracting and concentrating particles from bone marrow aspirate, the method comprising:
providing the bone marrow aspirate to a fluid exchange module of a microfluidic device;
providing an aqueous solution to the fluid exchange module of the microfluidic device, the fluid exchange module comprising a corresponding first microfluidic channel and a first array of island structures in the first microfluidic channel, the first array of island structures being arranged in one or more rows that extend along a longitudinal direction of the first microfluidic channel, each island structure in a row being spaced apart from an adjacent island structure in the row to form an opening, wherein the bone marrow aspirate and the aqueous solution are provided to the fluid exchange module under conditions such that particle-free portions of the bone marrow aspirate are shifted through the opening between adjacent island structures within a row, and an inertial lift force causes the particles in the bone marrow aspirate to cross streamlines and transfer into the aqueous solution;

passing, from the fluid exchange module, the aqueous solution containing the transferred particles, to a particle concentration module, the particle concentration module comprising a corresponding second microfluidic channel and a second array of island structures arranged in a row, each island structure within the second array of island structures being spaced apart from an adjacent island structure in the row to form an opening, wherein the aqueous solution containing the transferred particles is provided to the particle concentration module under conditions such that particle-free portions of the buffer solution are shifted through the opening between adjacent island structures within the second microfluidic channel, and such that the particles within the aqueous solution are focused to one or more streamlines within an inertial focusing section of the particle concentration module.

9. The method of claim 8, wherein the particles are nucleated cells.

10. The method of claim 9, wherein the nucleated cells are stem cells.

11. A method of isolating and concentrating particles from a biological fluid sample, the method comprising:

obtaining the biological fluid sample;

providing the biological fluid sample to a fluid exchange module of a microfluidic device;

providing a second fluid sample to the fluid exchange module of the microfluidic device, the fluid exchange module comprising a corresponding first microfluidic channel and a first array of island structures in the first microfluidic channel, the first array of island structures being arranged in one or more rows that extend along a longitudinal direction of the first microfluidic channel, each island structure in a row being spaced apart from an adjacent island structure in the row to form an opening, wherein the biological fluid sample and the second fluid sample are provided to the fluid exchange module under conditions such that a first portion of the biological fluid sample comprising particles are shifted through the opening between adjacent island structures within a row, and an inertial lift force causes the particles in the biological fluid sample to cross streamlines and transfer into the second fluid sample;

passing, from the fluid exchange module, the second fluid sample containing the transferred particles, to a particle concentration module, the particle concentration module comprising a corresponding second microfluidic channel and a second array of island structures arranged in a row, each island structure within the second array of island structures being spaced apart from an adjacent island structure in the row to form an opening, wherein the second fluid sample containing the transferred particles is provided to the particle concentration module under conditions such that particle-free portions of the second fluid sample are shifted through the opening between adjacent island structures within the second microfluidic channel, and such that a concentration of the particles within the second fluid sample increases;

further processing the transferred particles within the second fluid sample to provide a processed second fluid sample; and administering the second fluid sample containing the transferred and processed particles to a subject.

12. A method of isolating and concentrating particles from a first fluid sample, the method comprising:

providing the first fluid sample to a fluid exchange module of a microfluidic device;

providing a second fluid sample to the fluid exchange module of the microfluidic device, the fluid exchange module comprising a corresponding first microfluidic channel and a first array of island structures in the first microfluidic channel, the first array of island structures being arranged in one or more rows that extend along a longitudinal direction of the first microfluidic channel, each island structure in a row being spaced apart from an adjacent island structure in the row to form an opening, wherein the first fluid sample and the second fluid sample are provided to the fluid exchange module under conditions such that a first type of particles within the first fluid sample are shifted through the opening between adjacent island structures within a row, and an inertial lift force causes a second type of particles within the first fluid sample to cross streamlines and transfer into the second fluid sample; and passing, from the fluid exchange module, the second fluid sample containing the second type of particles, to a particle concentration module, the particle concentration module comprising a corresponding second microfluidic channel and a second array of island structures arranged in a row, each island structure within the second array of island structures being spaced apart from an adjacent island structure in the row to form an opening, wherein the second fluid sample containing the second type of particles is provided to the particle concentration module under conditions such that portions of the second fluid sample are shifted through the opening between adjacent island structures within the second microfluidic channel, and such that a concentration of the second type particles within the second fluid sample increases.

13. The method of claim 12, wherein an average size of the second type of particle is greater than an average size of the first type of particle.

14. The method of claim 12, wherein the first fluid sample comprises blood.

15. The method of claim 12, wherein the first type of particles comprises platelets, viruses, bacteria, or a combination thereof.

16. The method of claim 12, wherein the second type of particles comprises red blood cells, white blood cells or a combination of red and white blood cells.

17. The method of claim 12, wherein the second type of particle is bound to a bead.

18. The method of claim 17, wherein the second type of particle comprises a cell.

19. The method of claim 12, wherein the portions of the second fluid sample that are shifted through the opening between adjacent island structures within the second microfluidic channel are particle-free.

20. A method of isolating and concentrating particles from a first fluid sample, the method comprising:

providing the first fluid sample to a fluid exchange module of a microfluidic device;

providing a second fluid sample to the fluid exchange module of the microfluidic device, the fluid exchange module comprising a corresponding first microfluidic channel and a first array of island structures in the first microfluidic channel, the first array of island structures being arranged in one or more rows that extend along a longitudinal direction of the first microfluidic channel, each island structure in a row being spaced apart from an adjacent island structure in the row to form an opening, wherein the first fluid sample and the second fluid sample are provided to the fluid exchange module under conditions such that a first type of particles within the first fluid sample are shifted through the opening between adjacent island structures within a row, and an inertial lift force causes a second type of particles within the first fluid sample to cross streamlines and transfer into the second fluid sample; and passing, from the fluid exchange module, the first fluid sample containing the first type of particles, to a particle concentration module, the particle concentration module comprising a corresponding second microfluidic channel and a second array of island structures arranged in a row, each island structure within the second array of island structures being spaced apart from an adjacent island structure in the row to form an opening, wherein the first fluid sample containing the first type of particles is provided to the particle concentration module under conditions such that portions of the first fluid sample are shifted through the opening between adjacent island structures within the second microfluidic channel, and such that a concentration of the first type particles within the first fluid sample increases.

21. The method of claim 20, wherein an average size of the second type of particle is greater than an average size of the first type of particle.

22. The method of claim 20, wherein the first fluid sample comprises blood.

23. The method of claim 20, wherein the first type of particles comprises platelets, viruses, bacteria, or a combination thereof.

24. The method of claim 20, wherein the second type of particles comprises red blood cells, white blood cells or a combination of red and white blood cells.

25. The method of claim 20, wherein the portions of the first fluid sample that are shifted through the opening between adjacent island structures within the second microfluidic channel are particle-free.

* * * * *

UNITED STATES PATENT AND TRADEMARK OFFICE
CERTIFICATE OF CORRECTION

| | | |
|---|---|---|
| PATENT NO. | : 10,583,438 B2 | Page 1 of 1 |
| APPLICATION NO. | : 15/425818 | |
| DATED | : March 10, 2020 | |
| INVENTOR(S) | : Ravi Kapur, Kyle C. Smith and Mehmet Toner | |

It is certified that error appears in the above-identified patent and that said Letters Patent is hereby corrected as shown below:

In the Specification

Column 1, Line 14, insert -- STATEMENT OF FEDERALLY SPONSORED RESEARCH
This invention was made with government support under Grant Nos. EB002503, and EB012493 awarded by the National Institutes of Health. The government has certain rights in the invention. --

Signed and Sealed this
Twenty-third Day of May, 2023

Katherine Kelly Vidal
*Director of the United States Patent and Trademark Office*